United States Patent [19]

Lupski et al.

[11] Patent Number: 5,294,533
[45] Date of Patent: Mar. 15, 1994

[54] ANTISENSE OLIGONUCLEOTIDE ANTIBIOTICS COMPLEMENTARY TO THE MACROMOLECULAR SYNTHESIS OPERON, METHODS OF TREATING BACTERIAL INFECTIONS AND METHODS FOR IDENTIFICATION OF BACTERIA

[75] Inventors: James R. Lupski, Houston, Tex.; Leonard Katz, Waukegan, Ill.

[73] Assignees: Baylor College of Medicine, Houston, Tex.; Abbott Laboratories, Abbott Park, Ill.

[21] Appl. No.: 572,191

[22] Filed: Aug. 23, 1990

Related U.S. Application Data

[63] Continuation-in-part of Ser. No. 215,135, Jul. 5, 1988, abandoned.

[51] Int. Cl.$^5$ .................. C21Q 1/68; C12N 15/00; C12N 15/11
[52] U.S. Cl. ....................... 435/6; 435/172.3; 536/24.32
[58] Field of Search ............ 435/172.3, 6; 536/27, 536/24.32

[56] References Cited

U.S. PATENT DOCUMENTS

| | | | |
|---|---|---|---|
| 4,563,419 | 1/1986 | Ranki et al. | 435/6 |
| 4,652,517 | 3/1987 | Scholl et al. | 435/5 |
| 4,851,330 | 7/1989 | Kohne et al. | 435/6 |

OTHER PUBLICATIONS

Erickson et al., Gene, 40:67–78 (1985).
Wang et al., Nucleic. Acids Res., 14(10):4293–4307 (1986).
Wang et al., J. Biol. Chem., 260(6):3368–3372 (1985).
Inouye et al., J. Bacteriology, 172(1):80–85 (1990).

*Primary Examiner*—Richard A. Schwartz
*Assistant Examiner*—Nancy T. Vogel
*Attorney, Agent, or Firm*—Fulbright & Jaworski

[57] ABSTRACT

A method of interrupting the expression of a macromolecular synthesis operon in bacteria comprising the step of binding an antisense oligonucleotide to a single stranded DNA or to a mRNA transcribed from the macromolecular synthesis operon. The antisense oligonucleotide can be either sequence specific to a unique intergenic sequence or a sequence specific to a bacterial homologous sequence. By interrupting the expression of the macromolecular synthesis operon bacterial infections can be treated. Specific antisense oligonucleotides are disclosed. The ability of the antisense oligonucleotide to bind the mRNA or single stranded DNA also allows the identification of the bacteria by using a unique intergenic antisense oligonucleotide to bind to the single stranded DNA or to the mRNA transcribed from the macromolecular synthesis operon. A method for competitively inhibiting the protein products of the MMS operon with oligonucleotides is also disclosed. Methods of identifying unique intergenic sequence is also disclosed.

25 Claims, 20 Drawing Sheets

```
E. COLI        : MAGRIPRVFINDLLARTDIVDLIDARVKLKKQGKNFHACCPFHNEKTPSFTVNGEKQFYH
S. TYPHYMURIUM : ----------------------V-------------Y---------------------
B. SUBTILIS    : -GN---DEIVDQVQKSA--EV-GDY-Q-----R-YFGL----G-S----S-SPD--IF-

E. COLI        : CFGCGAHGNAIDFLMNYDKLEFVETVEELAAMHNLEVPFE.AGSGPSQIERHQRQTLYQL
S. TYPHYMURIUM : ----------------------------------------IY-.--T-L-----N----
B. SUBTILIS    : -----G--VFS--RQMEGYS-A-S-SH--DKYQIDF-DD1TVHSGARP-SSGE-KMAEA

E. COLI        : MDGLNTFYQQSL.QQPVATSARQYLEKRGLSHEVIARFAIGFAPPGWDNVLKRFGGNPEN
S. TYPHYMURIUM : ---N---D----.TH-A-KP--D--Q----A-I-Q----------A----N-SD----
B. SUBTILIS    : HEL-KK--HHL-INTKEGGE-LD---LS--FTK-L-NE-Q--Y-LDS--FIT-FLVKRGFS

E. COLI        : RQSLIDAGMLVTNDQGRSY.DRFRERVMFPIRDKRGRVIGFGGRVLGNDTPKYLNSPETD
S. TYPHYMURIUM : KAL-L-----N-E-ST-.----N----------------------------------
B. SUBTILIS    : EAQMEK--L-IRRED-SG-f----N-----H-HH-A-VA-S--A--SQQ---M-----P

E. COLI        : IFHKGRQLYGLYEAQQDNAEPNRLLVVEGYMDVVALAQYGINYAVASLGTSTTADHIQLL
S. TYPHYMURIUM : ------------------YS---Q-----D-------------------------MHM-
B. SUBTILIS    : L---SKL--NF-K-RLHIRKQE-AVLF--FA--YTAVSSDVKESI-TM---L-D--VKI-

E. COLI        : FRATNNVICCYDGDRAGRDAAWRA
S. TYPHYMURIUM : ------------------------
B. SUBTILIS    : R-NVEEI-L---S-K--YE-TLK-
```

FIG. 6D

ANTISENSE OLIGONUCLEOTIDE ANTIBIOTICS COMPLEMENTARY TO THE MACROMOLECULAR SYNTHESIS OPERON, METHODS OF TREATING BACTERIAL INFECTIONS AND METHODS FOR IDENTIFICATION OF BACTERIA

This application is a continuation-in-part of U.S. application Ser. No. 215,135, filed Jul. 5, 1988, now abandoned.

FIELD OF THE INVENTION

The present invention relates generally to antisense oligonucleotides which bind to a messenger RNA and single strand DNA. More particularly it relates to antisense oligonucleotides which bind to messenger RNA transcribed from the macromolecular synthesis operon of bacteria. It also relates to the treatment of bacterial infections by the introduction of antisense oligonucleotides into bacteria. It further relates to the method of identification of bacteria by the binding of an antisense oligonucleotide specifically to a unique sequence in the intergenic regions of the macromolecular synthesis operon of bacteria. It also relates to the treatment of bacterial infections by competitive inhibition of the macromolecular synthesis operon gene products by utilizing oligonucleotides known to act as recognition sequences for the MMS operon protein products. It also relates to identification of bacteria. It further relates to the isolation and identification of unique intergenic sequences.

BACKGROUND OF THE INVENTION

It has been demonstrated that the genes involved in initiating the synthesis of DNA, RNA and protein in bacteria are contained in one single structural unit named the macromolecular synthesis operon (MMS). The genes are part of a single transcription unit and have been identified as rpsU encoding ribosomal protein S21 involved in initiating translation, dnaG encoding the protein primase which initiates DNA replication and rpoD which encodes sigma-70 involved in initiating transcription. The operon structure is found in both gram negative bacteria, such as *Escherichia coli* and *Salmonella typhimurium*, and in gram positive bacteria such as *Bacillus subtilis*. The individual structural genes are conserved and have large areas of homology. On the other hand, the intergenic sequences between the structural gene within the operon are unique to each bacterial species. The MMS operon appears to be a central information processing unit for directing the flow of genetic information. The organization of the operon suggests that under certain physiological conditions there is a need for coordination of synthesis of the information macromolecules (DNA, RNA and protein) in the cell and hence a coregulation of the initiator genes. Since the synthesis of each class of macromolecule appears to be regulated at its initiation step, regulation of the MMS operon most likely plays a role in regulating cell growth.

The MMS operon contains three structural genes. The rpsU gene encodes the ribosomal protein S21 which is required for specific initiation of messenger RNA (mRNA) translation. The protein S21 interacts with a stretch of ribosomal RNA (rRNA) complementary to the mRNA ribosomal binding site called the Shine-Dalgarno sequence located at the 3' end of the 16S rRNA. Colicin E3 removes 50 nucleotides from the 3' terminus of 16S rRNA. E3 treated ribosomes cannot carry out polypeptide chain initiation nor chain elongation. In reconstitution experiments, E3 treated ribosomes bind all 30S proteins except S21. RNA protein cross-linking experiments demonstrate that protein S21 is cross-linked to the 3' dodecanucleotide of the 16S rRNA. The base-pairing potential of the 3' terminus of 16S rRNA depends on the functional state of the 30S subunit and the presence of S21, which is required for specific initiation of *E. coli* and phage MS2 mRNA translation.

Initiation of DNA replication requires a priming RNA which is synthesized by the dnaG gene product, primase. This protein binds to the phage G4 origin of replication. Primase also is known to interact with the multienzyme complex primosome to initiate synthesis of Okazaki fragments on the chromosomal replication fork-lagging strand of *E. coli*. Primase is the sole priming enzyme required for initiation of DNA replication at the origin of the *E. coli* chromosome. A parB mutation in the dnaG gene results in abnormal partition of chromosomes and was originally isolated as a thermosensitive mutant affecting DNA synthesis and cellular division. Thus, in addition to initiation of DNA replication, the dnaG gene appears to play some role in regulating cell division.

The ropD gene product sigma-70 is involved in the recognition of promoter sequences for the specific initiation of RNA transcription. Sigma-70 interacts with the core polymerase $\alpha_2\beta\beta''$ conferring specificity for promoter sequences. Sigma-70 is a member of a large family of RNA polymerase sigma factors. Thus, the macromolecular synthesis operon gene products share a common mechanism. Through protein-nucleic acid interactions the gene products of the MMS operon bind specific nucleotide sequences. For example S21 binds the Shine-Dalgarno sequence/ribosome binding site, primase binds the origin of replication, and sigma-70 binds a promoter sequence. These interactions result in initiation of synthesis of protein, DNA or RNA respectively.

Antisense RNAs have been utilized both in nature and experimentally to regulate gene expression. For example antisense RNA is important in plasmid DNA copy number control, in development of bacteriophage P22. Antisense RNAs have been used experimentally to specifically inhibit in vitro translation of mRNA coding from Drosophila hsp23, to inhibit Rous sarcoma virus replication and to inhibit 3T3 cell proliferation when directed toward the oncogene c-fos. Furthermore, it is not necessary to use the entire antisense mRNA since a short antisense oligonucleotide can inhibit gene expression. This is seen in the inhibition of chloramphenicol acetyltransferase gene expression and in the inhibition of specific antiviral activity to vesicular stomatitis virus by inhibiting the N protein initiation site. Antisense oligonucleotides to the c-myc onocogene have been demonstrated to inhibit entry into the S phase but not the progress from $G_0$ to $G_1$. Finally, inhibition of cellular proliferation has been demonstrated by the use of antisense oligodeoxynucleotides to PCNA cyclin.

Antibiotics are important pharmaceuticals for the treatment of infectious diseases in a variety of animals including man. The tremendous utility and efficacy of antibiotics results from the interruption of bacterial (prokaryotic) cell growth with minimal damage or side effects to the eukaryotic host harboring the pathogenic organisms. All antibiotics destroy bacteria by interfering with the normal flow of genetic information. This is performed by inhibition of any one of the following: DNA replication, that is, DNA to DNA (for example, the drugs Novobiocin and Nalidixic acid); transcription, that is, DNA to RNA (for example, Rifampin); translation, that is, RNA to protein (for example, tetracyclines, erythromycin and kanamycin); or cell wall synthesis (for example, penicillins).

The present invention provides a new class of antibiotics and a method for the treatment of bacterial infections either generally or specifically. The antibiotics are antisense oligonucleotide sequences which bind mRNA transcribed from the MMS operon. This is a new method of treating bacterial infections by interfering with the fundamental structural unit that regulates the growth and replication of bacteria.

SUMMARY OF THE INVENTION

An object of the present invention is the provision of a method for the treatment of bacterial infections.

An additional object of the present invention is the use of antisense oligonucleotides to treat bacterial infections.

A further object of the present invention is a method for identifying bacteria.

Another object of the present invention is the provision of a sequence which detects the presence or absence of bacteria.

An additional object of the present invention is the provision of antibiotics which interrupt the operation of the macromolecular synthesis operon in bacteria.

A further object of the present invention is the use of competitive inhibitors to interfere with the nucleotide recognition site of the macromolecular synthesis operon gene products.

An additional object of the present invention is a method of determining unique intergenic sequences in the macromolecular synthesis operon.

Thus, in accomplishing the foregoing objects there is provided in accordance with one aspect of the present invention a method of interrupting the expression of a macromolecular synthesis operon comprising the step of hybridizing an antisense oligonucleotide to a mRNA transcribed from said macromolecular synthesis operon. The antisense oligonucleotide sequence can be specific to a unique intergenic sequence in the mRNA or it can be a sequence which is specific to a region of the mRNA containing a sequence which is homologous between bacterial strains or any combination of these.

A further aspect of the present invention is the method for treating bacterial infections by interrupting the expression of the macromolecular synthesis operon by binding an antisense oligonucleotide antibiotic to a mRNA transcribed from the macromolecular synthesis operon.

In preferred embodiments, the antisense oligonucleotide antibiotic can be selected from the following sequences:

5' CAITGCTTTGGITGIGGIGCGIIIGGCAA 3',
5' TTGCCIIICGCICCCICAICCAAAGCAITG 3',
5' CANTGCTTTGGNTGNGGNGCGNNNGGCAA 3',
5' TTGCCNNNCGCNCCNCANCCAAAGCANTG 3',
5' ACITAIGCIACITGGTGGATGIGICAGGC 3',
5' ACNTANGCNACNTGGTGGATCNGNCAGGC 3',
5' GCCTGICIGATCCACCAIGTIGCITAIGT 3',
5' GCCTGNCNGATCCACCANGTNGCNTANGT 3',
5' TTIGCTTCGATITGICGIATACG 3',
5' TTNGCTTCGATNTGNCGNATACG 3',
5' ACGAGCCGTTCGACGTAGCTCTGCG 3',
5' CGGCGTGCGTTTTCGCGAGCCAGT 3',
5' ACATGCCGGTAATTAAAGTACGTG 3',
5' CATCCAAAGCAGTGGTAAAACTGTTT 3',
5' TCACCGATCGGCGTTTCCA 3', 5' GGCCCCGATTTTTAGCAA 3',
5' CTTGCGTAAGCGCCGGGG 3' and 5' TATTCGATGCTTTAGTGC 3'.

Another aspect of the present invention is a method for typing or identifying bacteria comprising the steps of binding a unique intergenic antisense oligonucleotide to a mRNA transcribed from the macromolecular synthesis operon or the macromolecular synthesis operon DNA and then determining the amount of binding between the species specific macromolecular synthesis oligonucleotide and the mRNA transcribed from the macromolecular synthesis operon of a given bacterial species.

A further aspect of the present invention is the use of a homologous sequence to detect the presence or absence of bacteria.

In the treatment of a bacterial infection or in the identification of bacteria the antisense oligonucleotide is at least 10 nucleotides (10 mer). In a preferred embodiment, an oligonucleotide of 16 to 29 mer is used.

An additional aspect of the present invention is the provision of an antisense oligonucleotide antibiotic of at least 10 nucleotides, wherein said oligonucleotide binds to a mRNA transcribed from a macromolecular synthesis operon. In one embodiment the antibiotic further comprises a carrier molecule linked to the oligonucleotide for facilitating the uptake of the oligonucleotide into the bacterium. The carrier molecule can be an amino acid, and in one preferred embodiment is leucine. In another embodiment the 3' and/or 5' termini of the oligonucleotide is derivatized to prevent the degradation, e.g. by exonucleases, of the oligonucleotide after bacteria uptake.

Other and further objects, features and advantages will be apparent from the following description of the presently preferred embodiments of the invention given for the purpose of disclosure when taken in conjunction with the accompanying drawings.

The drawings are not necessarily to scale and certain features of the invention may be exaggerated in scale or shown in schematic form in the interest of clarity and conciseness.

DETAILED DESCRIPTION

It will be readily apparent to one skilled in the art that various substitutions and modifications may be made to the invention disclosed herein without departing from the scope and spirit of the invention.

The rpsU-dnaG-rpoD macromolecular synthesis operon (MMS) is conserved throughout different bacterial species. Further, the gene order and organization of the operon is conserved in all bacteria.

Figure 1:
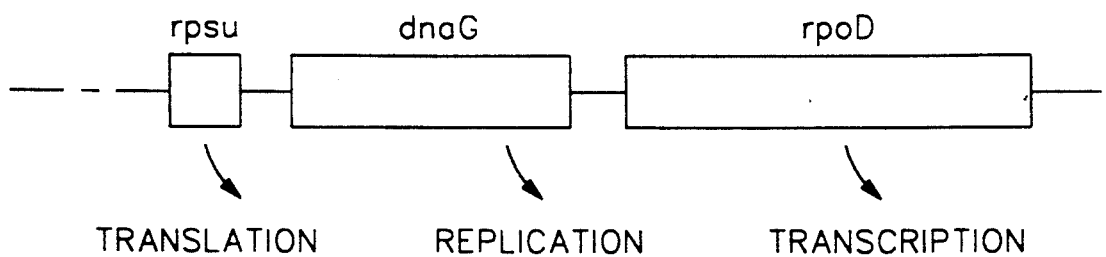
FIG. 1 is the macromolecular synthesis operon shown in schematic form. It contains three genes, one each, involved in the initiation of translation (rpsU), replication (dnaG) and transcription (rpoD).

The MMS operon includes genes involved in initiating: translation, rpsU; replication, dnaG; and transcription, rpoD. These genes are contained within a single transcriptional unit, FIGS. 1 and 2, and are involved in initiating synthesis of the major information macromolecules of the cell: DNA, RNA and protein. The organization of the operon suggests that under certain physiological conditions there is a need for coordination of synthesis of DNA, RNA and protein in the cell and hence a coregulation of the initiator genes. Since the synthesis of each class of information macromolecule (DNA, RNA and protein) appears to be regulated at its initiation step, regulation of the MMS operon most likely plays a role in regulating cell growth.

In the MMS operon cis-acting regulatory sequences can occur within the coding regions. In gram-negative bacteria these include the nut$_{eq}$ site within the rpsU structural gene and promoters P$_a$, P$_b$, and P$_{hs}$ in the dnaG structural gene. Promoter P$_3$ of the *B. subtilis* MMS operon is within the gene coding for P23. Other cis-acting regulatory sequences are located in the intergenic regions; terminator T$_1$ is located between rpsU and dnaG and an RNA processing site occurs in the dnaG-rpoD intergenic sequences. Thus, multiple cis-acting regulatory sequences allow discoordinate regulation as well as differential relative rates of individual gene expression within this operon structure.

Codon usage can affect relative amounts of individual gene expression. The presence of codon preference reflects the relative concentrations of isoaccepting tRNA species in the cell. The use of rare codons provides a means to ensure low level expression of regulatory genes. The dnaG gene contains greater than ten times the number of rare triplet codons as other *E. coli* genes and the absolute number of rare codons in the dnaG mRNA is similar to that of other control genes (e.g. lacI, trpR). Rare codons also occur in the *S. typhimurium* dnaG mRNA and the dnaE gene of *B. subtilis*. The dnaG gene is equivalent to the dnaG gene, each encodes the primase protein which initiates DNA replication. An additional translational regulatory mechanism operative in the MMS operon relies on the occurrence of ribosome binding sites with varying degrees of complementarity to the Shine-Dalgarno sequence. This can be seen in the *E. coli* dnaG gene, and is presumably due to the difference in free energy of binding leading to less efficient binding of the ribosome to the dnaG portion of the MMS mRNA. Both of these translational regulatory mechanisms, rare codon usage and altered ribosome binding affinity may partially explain the observed apparent discoordination of expression of the genes in this operon. The steady state relative abundances for the MMS operon protein products in the *E. coli* cell are 40,000 for S21, 50 for primase and approximately 3000 for sigma-70.

Figure 3:
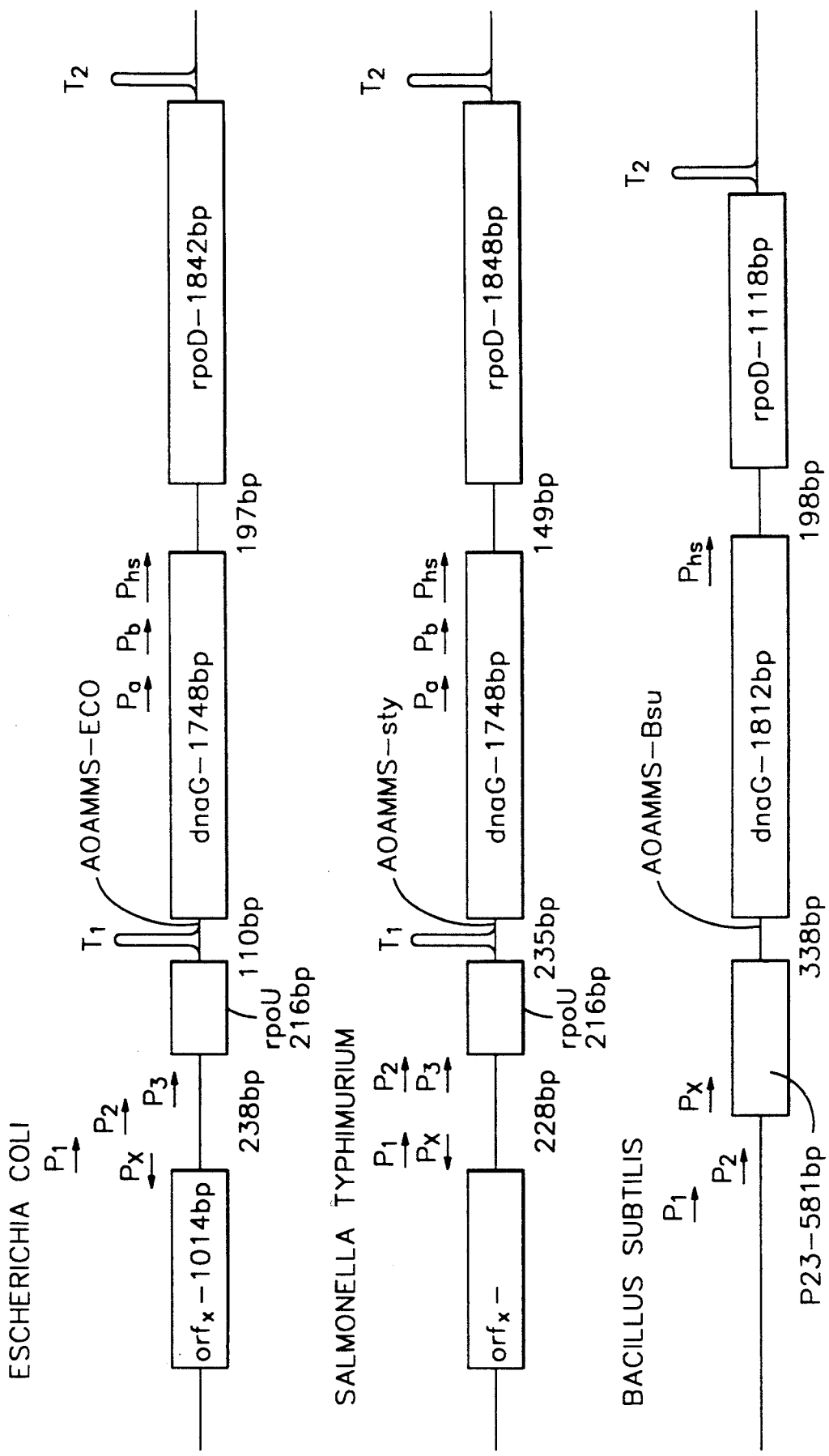
FIG. 3 is a comparison of the macromolecular synthesis operon in different species, *E. coli, S. typhimurium* and *B. subtilis*. The genes are depicted by open boxes with the size given in base pairs (bp) including termination codon. The size of the intergenic sequences is given below. Position of promoters (P) are denoted. AOAMMS—Eco is complementary to the *E. coli* macromolecular synthesis operon rpsU-dnaG intergenic sequences. AOAMMS—Sty is complementary to the *S. typhimurium* macromolecular synthesis operon rpsU-dnaG intergenic sequences. AOAMMS—Bsu is complementary to the *B. subtilis* macromolecular synthesis operon P23-dnaE intergenic sequences.

Comparative analysis of three sequenced MMS operons reveals several interesting features (FIG. 3). All of the operons contain three open reading frames and transcription of the operon is initiated by several promoters at the 5' end. The major promoters have overlapping nucleotide sequences ($-10$ and $-35$ regions) and the cis-acting regulatory sequences appear to be clustered in small regions. Each operon contains a heat shock promoter (P$_{hs}$) within the DNA replication initiation gene, dnaG or dnaE. The *E. coli* and *S. typhimurium* operons contain an open reading frame (orf$_x$) upstream of the external promoters (P$_1$, P$_2$, P$_3$). Only 7 bp separate the $-35$ sequences of P$_x$ and P$_1$ in *E. coli* while these sequences actually overlap in the *S. typhimurium* operon.

Figure 6A:
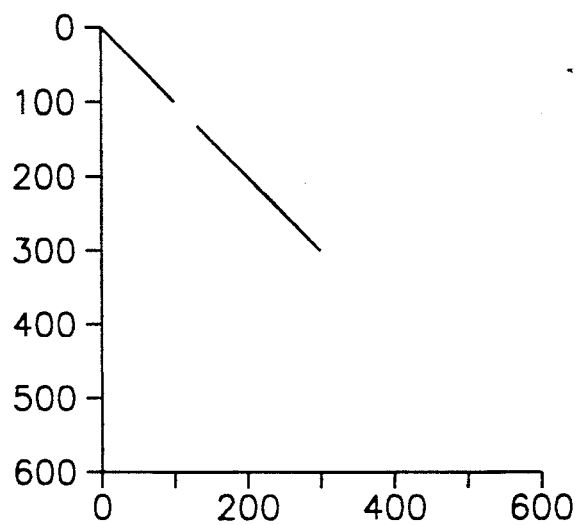
FIG. 6 (parts A-D) shows the homologies between bacterial strains for the primase gene. The information was generated from DNA sequences in GenBank utilizing the Molecular Biology Information Resources Multialign program to optimize homology searches of protein sequence data. The data is aligned from left to right on the abscissa, the amino terminal to the carboxy terminal portions of the protein. The numbers represent the amino acid positions in the protein primary sequence. In (a) *B. subtilis* was compared to *E. coli*, while in (b) *S. typhimurium* was compared to *E. coli*, and in (c) *B. subtilis* is compared to *S. typhimurium*. In (d), the *S. typhimurium* and *B. subtilis* primase protein sequences have been aligned to the *E. coli* dnaG primase in the amino terminal region. Upper case letters represent aligned non-identical amino acids while lower case letters signify non-aligned amino acids. The dashes represent aligned identical bases while the dots signify gaps. The data demonstrate that the primase proteins are related and share homology domains particularly in the amino terminal regions. The nucleotide sequence encoding these areas of amino acid homology are also very homologous.
Figure 6B:
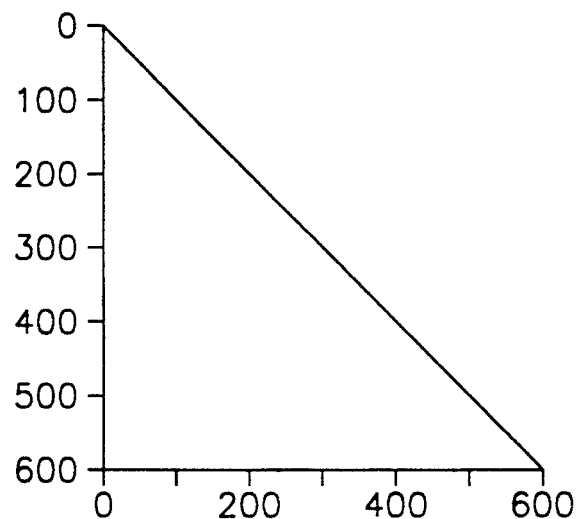
Figure 6C:
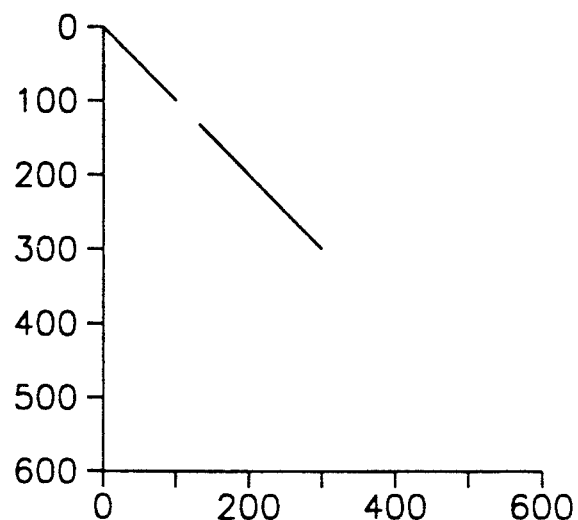

The central gene in the MMS operon is the one involved in initiating DNA replication. The dnaG gene product, primase has several activities which include (i) a protein-protein interaction with the primosome complex, (ii) a protein-nucleic acid interaction for recognition of the origin, (iii) an RNA polymerase activity to synthesize the primer RNA and (iv) a role in the partitioning of chromosomes as suggested by the parB mutation in the dnaG gene. There are no promoters which transcribe the dnaG gene directly. A 5' transcription terminator, poor ribosome binding site, occurrence of rare codons and clustering of rare codons are all mechanisms that maintain low level expression of this gene. Overexpression of the dnaG gene from a regulated promoter on an autonomously replicating plasmid kills the host cells. Evidence that regulation of dnaG expression directly affects cell growth comes from Tn5 mutagenesis data. A cloned dnaG gene with the MMS operon promoters intact, on a multicopy plasmid slows the growth rate of the host cell harboring it. After insertion of Tn5 into the dnaG promoter regions, presumably leading to decreased dnaG gene expression, growth rates return to control levels demonstrating that an increased dnaG expression can affect growth. Isolation of the parB mutation also suggests a direct role for dnaG in chromosome partitioning, cell division, and therefore, bacterial cell growth. The primase proteins encoded by the DNA replication initiation genes from the three sequenced MMS operons contain several regions of homology (FIG. 6).

The MMS operon is under very complex regulatory control which, teleologically would be expected of a unit whose control is important to regulation of cell growth. In addition to the intrinsic complex regulation, the operon interacts with several global regulatory networks including heat shock, the stringent response, and SOS. This operon appears to have evolved ways to be regulated both as a single unit and as a group of independent units by strategic positioning of transcriptional and translational control signals. The fact that the operon is the same in *E. coli* and *S. typhimurium* and very similar in *B. subtilis* suggests there is a selective advantage to evolving such a structure.

The term "oligonucleotide" as used herein, defines a molecule comprised of more than three deoxyribonucleotides or ribonucleotides. Its exact length will depend on many factors relating to the ultimate function or use of the oligonucleotide. A fragment of a sequence is any molecule containing some smaller part of a larger molecule. A derivative of the molecule includes alterations or additions to the 3' or 5' termini substitution of a base by inosine or a degenerate code substitution.

The term "homologous sequence" as used herein, defines a sequence within the MMS operon which has been conserved in bacterial species such that the sequence is nearly identical among a variety of species. Thus, because of its homology, this sequence cannot be used to distinguish different types of bacteria from themselves. However, this sequence can be used to determine the presence or absence of bacteria or as a target to attack with a single agent and thus interfere with the MMS operon expression in a variety of bacterial species.

The term "unique intergenic sequences" as used herein, defines a section of non-coding DNA which is positioned between the rpsU-dnaG/E and dnaG/E-rpoD genes within the MMS operon. In FIG. 3 some examples of the location within the MMS operon of the unique intergenic sequences, AOAMMS-Sty, AOAMAS-Eco and AOAMMS-Bsu, are shown. These MMS operon intergenic sequences are unique for each different species of bacteria. Thus, a specific sequence will be characteristic for a specific species of bacteria. Because of this uniqueness, the intergenic sequences can be used to identify the bacteria or for targeting a specific agent to kill or interrupt the functioning of a specific bacteria.

The term "antisense" as used herein, defines an oligonucleotide the sequence of which is complementary to the sense strand of the MMS operon. An antisense oligonucleotide will hybridize or bind (form a complex by Watson-Crick base pairing) in a complementary fashion to the messenger RNA molecule which has been transcribed from the MMS operon, as well as to a single stranded DNA of the MMS operon. The antisense oligonucleotide can be designed to bind to either a unique intergenic sequence, a homologous sequence or a combination of both unique and homologous sequences.

The term "antibiotic" as used herein, means an antisense oligonucleotide capable of interfering with the MMS operon to slow down bacterial growth thereby arresting growth and provoking cell death.

"Derivitizing" the oligonucleotide means altering the structure of the oligonucleotide to perform a specific function (e.g. (1) an addition to the 3' or 5' end to increase uptake into the cell; (2) blocking the 3' or 5' end to prevent exonucleolytic breakdown). This procedure may provide a more functional and stable oligonucleotide when it is in the bacteria. For example, the 3' end can be derivitized by adding a phosphorothioate linked nucleotide.

In one embodiment of the present invention there is included a method of interrupting the expression of a MMS operon comprising the step of hybridizing an antisense oligonucleotide of at least 10 mer to an mRNA transcribed from the MMS operon. In this method the antisense oligonucleotide hybridizes to the mRNA which is transcribed from the MMS operon. After the antisense oligonucleotide hybridizes to the mRNA, the mRNA is unable to be translated into the proteins encoded by the MMS operon. In order to inactivate the mRNA, only a small segment of the mRNA must be bound to the antisense oligonucleotide.

One skilled in the art readily recognizes that the antisense oligonucleotide can be delivered to the bacteria by a variety of commonly used delivery systems. For example, nasal spray, intravenous or intramuscular or intrathecal injection, oral or suppository administration. The specific choice of method depends on the location of the bacteria and is well within the skill in the art to determine. A small, 10–29 mer, antisense oligonucleotide that is delivered to a bacteria, is rapidly transported into the bacterial cell. Additionally, by modifying the 3' or 5' ends of the antisense oligonucleotide the rate of uptake or the specificity of uptake can be adjusted.

The antisense oligonucleotide is selected from the group consisting of a sequence specific to a unique intergenic sequence, a sequence specific to a bacterial homologous expressed sequence and any combination thereof.

By hybridizing to a specific unique intergenic sequence encoded in the single stranded DNA or mRNA which has been transcribed from the MMS operon, the antibiotic is targeted to interrupt and kill a specific type of bacteria. On the other hand, by hybridizing to the homologous sequence, the antibiotic is targeted to kill a wide variety of bacteria, i.e., all bacteria containing the homologous sequence. Depending on the length of the oligonucleotide or the location of the mRNA which is bound, the oligonucleotide may overlap and bind to both a unique sequence and a homologous sequence.

The exact length of the oligonucleotide needed to inhibit the functioning of the mRNA is at least 10 nucleotides (10 mer). In the preferred embodiment of the present invention, the oligonucleotide is in the range of 16 to 29 mer.

An additional aspect of the present invention is a method for treating bacterial infections comprising the step of interrupting the expression of a MMS operon by hybridizing an antibiotic to a mRNA transcribed from said MMS operon. The antibiotic can hybridize to either a homologous sequence, a unique intergenic sequence or a combination thereof.

Some examples of sequences which are used to bind to the mRNA to interrupt the function of the MMS operon and thus to treat bacterial infections are seen in Tables 1 and 2.

TABLE 1

Homologous Sequences Which Bind to mRNA Transcribed From the MMS Operon or to Single-Stranded Bacterial DNA Containing the MMS Operon

| | |
|---|---|
| MMS ALL1I | 5' CAITGCTTTGGITGIGGIGCGIIIGGCAA 3' |
| MMS ALL1I-R | 5' TTGCCIIICGCICCICAICCAAAGCAITG 3' |
| MMS ALL1D | 5' CANTGCTTTGGNTGNGGNGCGNNNGGCAA 3' |
| MMS ALL1D-R | 5' TTGCCNNNCGCNCCNCANCCAAAGCANTG 3' |
| MMS ALL2I | 5' ACITAIGCIACITGGTGGATGIGICAGGC 3' |
| MMS ALL2D | 5' ACNTANGCNACNTGGTGGATCNGNCAGGC 3' |
| MMS ALL3I | 5' GCCTGICIGATCCACCAIGTIGCITAIGT 3' |
| MMS ALL3D | 5' GCCTGNCNGATCCACCANGTNGCNTANGT 3' |
| MSS ALL4I | 5' TTIGCTTCGATITGICGIATACG 3' |
| MMS ALL4D | 5' TTNGCTTCGATNTGNCGNATACG 3' |
| MMS RPSU1 | 5' ACGAGCCGTTCGACGTAGCTCTGCG 3' |
| MMS RPSU2 | 5' CGGCGTGCGTTTTCGCGAGCCAGT 3' |
| MMS RPSU-5'ATG | 5' ACATGCCGGTAATTAAAGTACGTG 3' |
| (AOAMMS-dnaG) | 5'CATCCAAAGCAGTGGTAAAACTGTTT 3' |
| (AOAMMS-rpoD) | 5'TCACCGATCGGCGTTTCCA 3' |

TABLE 2

Unique Intergenic Sequences Which Bind to mRNA Transcribed from the MMS Operon or to Single-Stranded Bacterial DNA Containing the MMS Operon

| Abbreviation | Sequence | Bacterial Source |
|---|---|---|
| MMS BS1 | 5' GGGATTTGCACTAAAGCATCG 3' | B. subtilis |
| MMS BS2 | 5' GATCGCTTAACCTCATCATG 3' | B. subtilis |
| AOAMMS-Bsu | 5' TATTCGATGCTTTAGTGC 3' | B. subtilis. |
| MMS CHLAM1 | 5' GTCGGTGTAGGAAGTTTTTCTAGGGCCG 3' | C. trachomatis |
| MMS EC1 | 5' TTATCGTTGGCGGTAAACAACCGTTGG 3' | E. coli |
| AOAMMS-Eco | 5' GGCCCCGATTTTTAGCAA 3' | E. Coli |
| MMS HRDB1 | 5' CCACGCGGATTGGGCGTAACGCTCTTGGG 3' | S. coelicolor |

TABLE 2-continued

Unique Intergenic Sequences Which Bind to mRNA Transcribed from the MMS Operon or to Single-Stranded Bacterial DNA Containing the MMS Operon

| Abbreviation | Sequence | Bacterial Source |
|---|---|---|
| MMS HRDB1-R | 5' CCCAAGAGCGTTACGCCCAATCCGCGTGG 3' | S. coelicolor |
| MMS LIST1 | 5' CGTGTCATGCTCGAAATCGTCCAACTC 3' | L. monocytogenes |
| MMS MYXX1 | 5' CGCCCATGCAACCGGTTTGAGTTCGCG 3' | M. xanthus |
| MMS ST1A | 5' CGGCGCTTACGCAAGTCAGCGACA 3' | S. typhimurium |
| MMS ST2B | 5' CGACAGCTATACCGTCGACACC 3' | S. typhimurium |
| AOAMMS-Sty | 5' CTTGCGTAAGCGCCGGGG 3' | S. typhimurium |

The sequences in Table 1 bind to bacterial homologous sequences and thus kill a wide variety of bacterial species. These sequences are useful in treating a wide class of bacterial infections, since they attack both gram positive and gram negative bacteria.

The sequences in Table 2 are unique intergenic sequences which bind to specific sequences in specific bacteria. Employing an antisense alogonucleotide from Table 2 as an antibiotic will specifically inhibit the MMS operon of the bacteria for which it is specific, while not attacking the MMS operon of other bacteria. Each sequence in Table 2 is followed by the type of bacteria which is sensitive to the sequence. Employing these unique antisense oligonucleotides uses a specific antibiotic to kill a specific bacteria. Thus, the treatment to kill or interfere with the reproduction of specific bacterial species is targeted.

In the preferred embodiment, using unique sequences, the nucleotide sequence of the proposed antisense oligonucloetide antibiotics is complementary to the intergenic region of the 5' side of the DNA replication initiation gene (dnaG or dnaE) (see FIG. 3). This region of the MMS operon is chosen because the replication initiation gene has the lowest level of expression within the operon. Furthermore, in E. coli and S. typhimurium, this gene is located downstream from a terminator and is not directly transcribed by any promoter. In order to provide a more stable ineraction with the mRNA, the primary sequences of the antisense oligonucleotide are chosen to maximize GC base pairing. However, one skilled in the art recognizes that there is a balance between maintaining the uniqueness of the sequence and maximizing the GC base pairing.

Another embodiment of the invention is a method of identifying bacteria comprising the steps of hybridizing a known species specific unique intergenic antisense oligonucleotide to a mRNA transcribed from a MMS operon or a single stranded DNA and measuring the amount of said hybridization to determine the type of bacteria. The unique sequence will only hybridize to a specific bacteria species, therefore no hybridization indicates a different species and hybridization indicates the species with the specific sequence. Each bacterial species contains a MMS operon with a unique intergenic sequence which can be used to uniquely identify each species. The mRNA which is transcribed from the MMS operon spans the whole operon and contains the homologous and unique intergenic sequences. By designing oligonucleotides which bind to the unique intergenic sequences, the diagnosis and treatment can be tailored to only identify and interfere with the functioning of a MMS operon in those bacterial species which have that unique sequence. Thus, by using a variety of antisense oligonucleotide probes, bacteria can be typed for each individual species. The amount of hybridization can be determined by a variety of methods known to those skilled in the art, including radioisotopes, enzymes, fluorescers, antibodies and chemiluminescers. For example, the unique species specific intergenic antisense oligonucleotides can be labelled with biotin and then identified by a Strep avidin complex or a fluorescent tag.

The antisense oligonucleotides of Table 2 can be used to identify those bacteria which are listed after each antisense oligonucleotide sequence. One skilled in the art will readily recognize that as additional MMS operon intergenic sequences are sequenced, the present invention can be used to identify additional bacteria by antisense oligonucleotides synthesized to the unique intergenic sequences.

In bacteria typing, the length of the antisense oligonucleotide will be determined by the size necessary to bind specifically to the unique sequence. The oligonucleotide should be at least 10 nucleotides in length. In a preferred embodiment the sequences are between 16 and 29 mer. Examples of some preferred sequences are found in Table 2.

Figure 4:
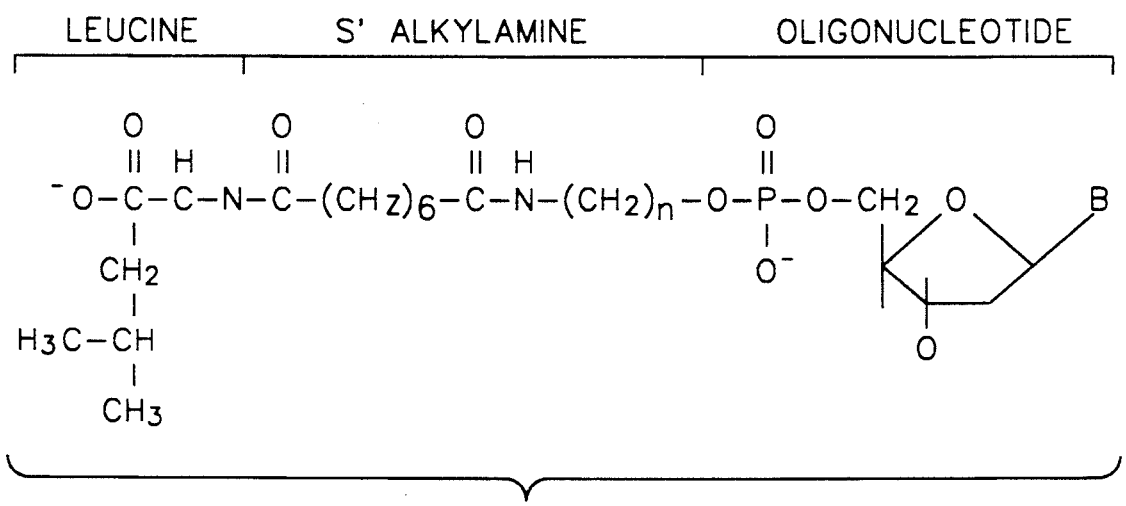
FIG. 4 shows a 5' modified antisense oligonucleotide antibiotic containing the addition of leucine.

In order for the antisense oligonucleotide antibiotic to effectively interrupt the MMS operon function by hybridizing to the mRNA transcribed from the MMS operon, the antisense oligonucleotide antibiotic must enter the bacterial cell. Although oligonucleotides are taken up by bacterial cells, some modification of the oligonucleotides can help facilitate or regulate uptake. Thus, a carrier molecule, for example an amino acid, can be linked to the oligonucleotide. In FIG. 4, the oligonucleotide is modified at the 5' end by adding a leucine molecule to the oligonucleotide. Bacteria have multiple transport systems for the recognition and uptake of molecules of leucine. The addition of this amino acid to the oligonucleotide facilitates the uptake of the oligonucleotide in the bacteria and does not interfere with the binding of the antisense oligonucleotide to the mRNA molecule.

One skilled in the art will readily recognize that other methods are available for facilitating the uptake of the antisense oligonucleotide antibiotic in the bacteria and for increasing the stability of oligonucleotides once inside the bacteria. For example, addition of other amino acids or peptides or primary amines to the 3' or 5' termini enables utilization of specific transport systems and inhibits cellular nuclease attack. Addition of lactose to the oligonucleotide by a covalent linkage can enable transport by lactose permease (product of the lac operon Y gene). Other sugar transport systems, known to be functional in bacteria, can be utilized to facilitate uptake into the bacterial cell.

Figure 5:
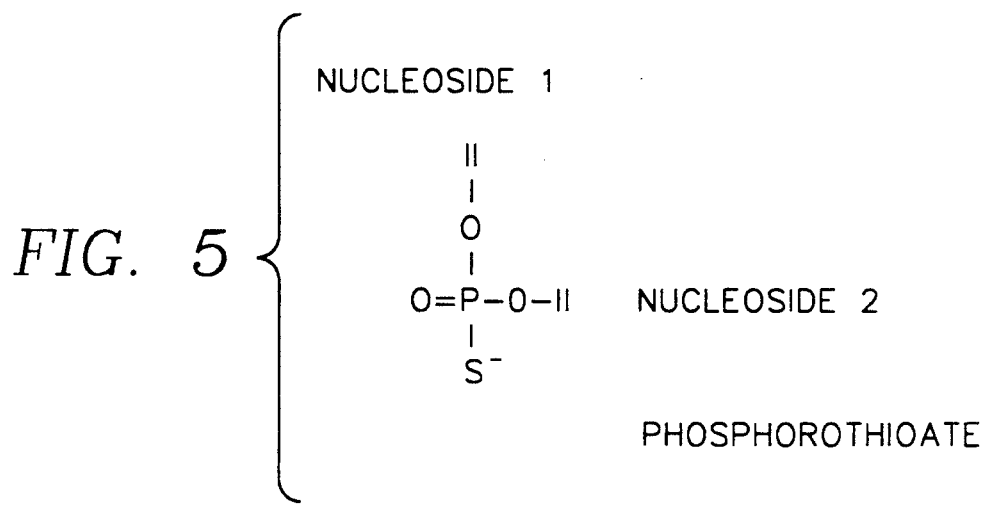
FIG. 5 shows a 3' modified antisense oligonucleotide antibiotic.

Once an oligonucleotide with or without the carrier has entered the bacterial cell, it is important that it remain stable for the time period necessary to bind to the mRNA transcribed by the MMS operon. In one embodiment of the present invention, the oligonucleotide is derivatized at the 3' end to prevent degradation of the oligonucleotide (FIG. 5). Other methods are known to alter the 3' and/or 5' ends of oligonucleotides to prolong the intracellular life and thus increase the availability for binding to the mRNA. For example, the addition of a primary amine to the 3' or 5' termini inhibits exonuclease activity and increases the cell life of antisense oligonucleotides.

The expressed sequences or genes, rpsU, dnaG, and rpoD, within the MMS operon have regions that are conserved or homologous in all bacteria. These conserved homologous regions are utilized to identify the presence or absence of any bacteria by hybridizing an antisense ologonucleotide that identifies the conserved homologous sequences.

The intergenic regions are DNA sequences between the expressed sequences rpsU-dnaG and dnaG-rpoD. Intergenic sequences have not been conserved and thus are unique to a given bacterial species. Thus, these unique intergenic sequences are useful in identifying a particular species of bacteria.

Species specific unique intergenic sequences from the macromolecular synthesis operon were obtained from the dnaG-rpoD or the rpsU-dnaG regions. Examples of homologous and unique sequences are the dnaG, rpoD and dnaG-rpoD, respectively, sequences from *L. monocytogenes* Tables 3 and 4 and the rpsU, dnaG and rpsU-dnaG, respectively, sequences from *H. influenzae* Table 5.

TABLE 3

*L. monocytogenes* DNA sequence including the dnaG carboxy terminus (numbered 1 to 282), dnaG-rpoD intergenic region (numbered 283 to 461) and the rpoD amino terminus (numbered 462 to 1043).

| GCA | ACT | TCT | TGG | TGC | AAC | ATC | GTT | TAT | CAT | GAT | AAT | 36 |
| Ala | Thr | Ser | Trp | Cys | Asn | Ile | Val | Tyr | His | Asp | Asn | |
| 1 | | | | 5 | | | | | 10 | | | |

| TAC | AAA | GCG | CTT | TAT | ACC | TAT | CTA | ATT | GGT | TAT | TCT | 72 |
| Tyr | Lys | Ala | Leu | Tyr | Thr | Tyr | Leu | Ile | Gly | Tyr | Phe | |
| | | 15 | | | | | 20 | | | | | |

| TGG | CAG | AAG | GTA | ATG | ATG | CAG | ATC | CAA | CGG | AAA | TTT | 108 |
| Trp | Gln | Lys | Val | Met | Met | Gln | Ile | Gln | Arg | Lys | Phe | |
| 25 | | | | | 30 | | | | | 35 | | |

| ATG | GAT | AGT | GTT | CCT | GAT | GCT | ACA | ATG | AAA | GGA | CTT | 144 |
| Met | Asp | Ser | Val | Pro | Asp | Ala | Thr | Met | Lys | Gly | Leu | |
| | | | 40 | | | | | 45 | | | | |

| ATC | AGT | AGC | CTC | GAA | ATG | GTT | ATT | AGT | CCA | GAT | GAA | 180 |
| Ile | Ser | Ser | Leu | Glu | Met | Val | Ile | Ser | Pro | Asp | Glu | |
| | 50 | | | | | 55 | | | | | 60 | |

| CAA | GGT | AAA | ACA | CAG | TTT | GAA | GAC | TAT | ATT | AGA | AGT | 216 |
| Gln | Gly | Lys | Thr | Gln | Phe | Glu | Asp | Tyr | Ile | Arg | Ser | |
| | | | | 65 | | | | | 70 | | | |

| CTA | AAG | CGG | TTT | AAA | TTA | GAA | CAA | AAG | AAA | AAA | GAA | 252 |
| Leu | Lys | Arg | Phe | Lys | Leu | Glu | Gln | Lys | Lys | Lys | Glu | |
| | | 75 | | | | | 80 | | | | | |

| CTT | GAG | CAA | GAG | CTA | AGC | AAC | TTT | AAA | TCG | | | 282 |
| Leu | Glu | Gln | Glu | Leu | Ser | Asn | Phe | Lys | Ser | | | |
| 85 | | | | | 90 | | | | | | | |

| TGAAAATGAC AAAGATAACG AAATTCGTGT CATGCTCGAA | 322 |
| ATCGTCCAAC TCAACCGTCA GTTAAACAGC GGCCAATTGG | 362 |
| ATTAATAACG TTTTAAAACC GCTAAATGAT GGTATTATTA | 402 |
| CCTAAGAGAA GCCTTTTAAT AAGGTTAGCG GCATTTTGGA | 442 |
| AGGAGGAATA CAGGCAGTT | 461 |

| ATG | AGT | GAT | AAA | ACA | AAA | AAC | ACA | AAA | CCA | GTT | GCT | 497 |
| MET | Ser | Asp | Lys | Thr | Lys | Asn | Thr | Lys | Pro | Val | Ala | |
| | | | | 5 | | | | | 10 | | | |

| GAA | CTA | AGT | GTT | GAG | CAA | GTA | AAA | GAA | GCC | CTG | ATA | 533 |
| Glu | Leu | Ser | Val | Glu | Gln | Val | Lys | Glu | Ala | Leu | Ile | |
| | | 15 | | | | | 20 | | | | | |

| GAA | GAA | GGT | AAG | AAA | AAG | GGG | ATT | TTA | ACT | TAT | GCA | 569 |
| Glu | Glu | Gly | Lys | Lys | Lys | Gly | Ile | Leu | Thr | Tyr | Ala | |
| 25 | | | | | 30 | | | | | 35 | | |

| AAA | ATC | GCT | GCC | AGA | TTA | GCT | CCA | TTC | ACT | TTG | GAT | 605 |
| Lys | Ile | Ala | Ala | Arg | Leu | Ala | Pro | Phe | Thr | Leu | Asp | |
| | | | 40 | | | | | 45 | | | | |

TABLE 3-continued

*L. monocytogenes* DNA sequence including the dnaG carboxy terminus (numbered 1 to 282), dnaG-rpoD intergenic region (numbered 283 to 461) and the rpoD amino terminus (numbered 462 to 1043).

| TCC | GAT | CAA | ATG | GAT | GAG | TAT | TTA | GAA | CAT | GTT | GGT | 641 |
|---|---|---|---|---|---|---|---|---|---|---|---|---|
| Ser | Asp | Gln | MET | Asp | Glu | Tyr | Leu | Glu | His | Val | Gly | |
| | 50 | | | | | 55 | | | | | 60 | |

| GAA | GCA | GGA | ATT | GAA | GTT | TCT | GAC | GAT | GCA | GAT | GAT | 697 |
|---|---|---|---|---|---|---|---|---|---|---|---|---|
| Glu | Ala | Gly | Ile | Glu | Val | Ser | Asp | Asp | Ala | Asp | Asp | |
| | | | | 65 | | | | | 70 | | | |

| GAG | GAT | CCG | GAT | GAA | ACA | GAA | CTT | GTA | AAA | GAA | GAA | 713 |
|---|---|---|---|---|---|---|---|---|---|---|---|---|
| Glu | Asp | Pro | Asp | Glu | Thr | Glu | Leu | Val | Lys | Glu | Glu | |
| | | 75 | | | | | 80 | | | | | |

| ACC | GAA | TCC | TTT | GAT | TTA | ACA | GAT | ATG | AGT | GTA | CCA | 749 |
|---|---|---|---|---|---|---|---|---|---|---|---|---|
| Thr | Glu | Ser | Phe | Asp | Leu | Thr | Asp | MET | Ser | Val | Pro | |
| 85 | | | | | 90 | | | | | 95 | | |

| CCA | GGC | GTA | AAA | ATT | AAT | GAC | CCT | GTT | CGC | ATG | TAT | 785 |
|---|---|---|---|---|---|---|---|---|---|---|---|---|
| Pro | Gly | Val | Lys | Ile | Asn | Asp | Pro | Val | Arg | MET | Tyr | |
| | | | 100 | | | | | 105 | | | | |

| CTG | AAA | GAA | ATT | GGT | CGA | GTA | GAC | TTA | CTT | ACA | GCG | 821 |
|---|---|---|---|---|---|---|---|---|---|---|---|---|
| Leu | Lys | Glu | Ile | Gly | Arg | Val | Asp | Leu | Leu | Thr | Ala | |
| | 110 | | | | | 115 | | | | | 120 | |

| GAT | GAA | GAA | ATT | GCC | TTA | GCA | AAA | CGT | ATC | GAA | GCT | 857 |
|---|---|---|---|---|---|---|---|---|---|---|---|---|
| Asp | Glu | Glu | Ile | Ala | Leu | Ala | Lys | Arg | Ile | Glu | Ala | |
| | | | | 125 | | | | | 130 | | | |

| GGC | GAC | ATT | GAA | GCC | AAA | GGA | CGT | CTT | GCA | GAA | GCC | 893 |
|---|---|---|---|---|---|---|---|---|---|---|---|---|
| Gly | Asp | Ile | Glu | Ala | Lys | Gly | Arg | Leu | Ala | Glu | Ala | |
| | | 135 | | | | | 140 | | | | | |

| AAC | CTG | CGC | CTT | GTT | GTA | AGT | ATT | GCA | AAA | CGT | TAT | 929 |
|---|---|---|---|---|---|---|---|---|---|---|---|---|
| Asn | Leu | Arg | Leu | Val | Val | Ser | Ile | Ala | Lys | Arg | Tyr | |
| 145 | | | | | 150 | | | | | 155 | | |

| GTT | GGT | CGC | GGT | ATG | TTA | TTC | CTT | GAT | TTA | ATT | CAA | 965 |
|---|---|---|---|---|---|---|---|---|---|---|---|---|
| Val | Gly | Arg | Gly | MET | Leu | Phe | Leu | Asp | Leu | Ile | Gln | |
| | | | 160 | | | | | 165 | | | | |

| GAA | GGT | AAC | ATG | GGA | CTA | ATG | AAA | GCC | GTT | GAG | AAA | 1001 |
|---|---|---|---|---|---|---|---|---|---|---|---|---|
| Glu | Gly | Asn | MET | Gly | Leu | MET | Lys | Ala | Val | Glu | Lys | |
| | 170 | | | | | 175 | | | | | 180 | |

| TTC | GAC | TTC | AAT | AAA | GGA | TTT | AAA | TTC | AGT | ACC | TAT | 1037 |
|---|---|---|---|---|---|---|---|---|---|---|---|---|
| Phe | Asp | Phe | Asn | Lys | Gly | Phe | Lys | Phe | Ser | Thr | Tyr | |
| | | | | 185 | | | | | 190 | | | |

| GCA | ACG | | | | | | | | | | | 1043 |
|---|---|---|---|---|---|---|---|---|---|---|---|---|
| Ala | Thr | | | | | | | | | | | |

TABLE 4

*L. monocytogenes* DNA sequence of an internal segment of dnaG.

| A | AGC | TTA | ACG | GAA | GAA | CAT | GCA | GAT | TTA | ATT | AAA | CGG | 37 |
|---|---|---|---|---|---|---|---|---|---|---|---|---|---|
| | Ser | Leu | Thr | Glu | Glu | His | Ala | Asp | Leu | Ile | Lys | Arg | |
| | 1 | | | | 5 | | | | | 10 | | | |

| CTT | ACT | AAC | CGG | GCG | ATT | ATT | TGT | TAT | GAC | GGT | GAC | 73 |
|---|---|---|---|---|---|---|---|---|---|---|---|---|
| Leu | Thr | Asn | Arg | Ala | Ile | Ile | Cys | Tyr | Asp | Gly | Asp | |
| | | 15 | | | | | 20 | | | | | |

| AGA | GCC | GGA | ATT | GAA | GCA | GCC | TAT | AAG | GCG | GGC | ACG | 109 |
|---|---|---|---|---|---|---|---|---|---|---|---|---|
| Arg | Ala | Gly | Ile | Glu | Ala | Ala | Tyr | Lys | Ala | Gly | Thr | |
| 25 | | | | | 30 | | | | | 35 | | |

| CTT | CTA | GTT | GAA | CGG | AAT | CGT | TTA | GAT | GTT | TTT | GTT | 145 |
|---|---|---|---|---|---|---|---|---|---|---|---|---|
| Leu | Leu | Val | Glu | Arg | Asn | Arg | Leu | Asp | Val | Phe | Val | |
| | | | 40 | | | | | 45 | | | | |

| TTG | CAA | CTT | CCA | GCT | GGA | AAA | GAT | CCC | GAT | GAC | TTT | 181 |
|---|---|---|---|---|---|---|---|---|---|---|---|---|
| Leu | Gln | Leu | Pro | Ala | Gly | Lys | Asp | Pro | Asp | Asp | Phe | |
| | 50 | | | | 55 | | | | | | 60 | |

TABLE 4-continued

*L. monocytogenes* DNA sequence of an internal segment of dnaG.

| ATT | CGA | GCA | AGT | GGT | CCA | GAA | AAA | TTC | AAA | GAA | GTT | 217 |
|---|---|---|---|---|---|---|---|---|---|---|---|---|
| Ile | Arg | Ala | Ser | Gly | Pro | Glu | Lys | Phe | Lys | Glu | Val | |
| | | | | 65 | | | | | 70 | | | |

| TAT | AAG | CAA | CAA | CGA | TCG | ACT | TGG | ACA | GCT | TTT | AAA | 253 |
|---|---|---|---|---|---|---|---|---|---|---|---|---|
| Tyr | Lys | Gln | Gln | Arg | Ser | Thr | Trp | Thr | Ala | Phe | Lys | |
| | | 75 | | | | | 80 | | | | | |

| TTC | ATT | ATT | TAC | GTA | GAG | AAC | GTA | | | | | 277 |
|---|---|---|---|---|---|---|---|---|---|---|---|---|
| Phe | Ile | Ile | Tyr | Val | Glu | Asn | Val | | | | | |
| 85 | | | | | 90 | | | | | | | |

TABLE 5

*H. Influenzae.* DNA sequence including the rpsU gene (numbered 1 to 213), the rpsU-dnaG intergenic region (numbered 214 to 350) and the dnaG gene (numbered 351 to 548).

| ATG | CCG | GTA | ATT | AAA | GTA | CGT | CAA | AAC | GAA | TCA | TTT | 36 |
|---|---|---|---|---|---|---|---|---|---|---|---|---|
| Met | Pro | Val | Ile | Lys | Val | Arg | Gln | Asn | Glu | Ser | Phe | |

| GAC | GTA | GCT | TTA | CGT | CGT | TTC | AAA | CGC | TCT | TGC | GAA | 72 |
|---|---|---|---|---|---|---|---|---|---|---|---|---|
| Asp | Val | ala | Leu | Arg | Arg | Phe | Lys | Arg | Ser | Cys | Glu | |

| AAA | GCG | GGA | ATC | TTA | GCT | GAA | ATA | CGC | GCT | CGC | GAA | 108 |
|---|---|---|---|---|---|---|---|---|---|---|---|---|
| Lys | Ala | Gly | Ile | Leu | Ala | glu | Ile | Arg | Ala | Arg | Glu | |

| TTT | TAC | GAA | AAA | CCA | ACT | ACA | ATT | CGT | AAA | CGT | GAA | 144 |
|---|---|---|---|---|---|---|---|---|---|---|---|---|
| Phe | Tyr | Glu | Lys | Pro | Thr | Thr | Ile | Arg | Lys | Arg | Glu | |

| AAT | GCA | ACA | CTT | GCA | AAA | CGT | CAC | GCA | AAA | CGC | AAC | 180 |
|---|---|---|---|---|---|---|---|---|---|---|---|---|
| Asn | Ala | Thr | Leu | Ala | Lys | Arg | His | Ala | Lys | Arg | Asn | |

| GCT | CGC | GAA | AAC | HCH | CGC | AAT | ACC | CGT | TTA | TAC | | 213 |
|---|---|---|---|---|---|---|---|---|---|---|---|---|
| Ala | Arg | Glu | Asn | Ala | Arg | Asn | Thr | Arg | Leu | Tyr | | |

| TAATTTATAG | TATTTTCTGA | CTCGAGTTAA | GACAAACCGT | 253 |
|---|---|---|---|---|

| GAATCCTTTG | GACTCACGGT | TTTGTTACTT | TAAGGCACAA | 293 |
|---|---|---|---|---|

| CAAAAATCTA | CGCCAAAAAC | GACCGCACTT | TCACACCACG | 333 |
|---|---|---|---|---|

| ATCACGGAGG | CTCGACA | ATG | AAA | GGT | TCT | ATT | CCA | CGC | 371 |
|---|---|---|---|---|---|---|---|---|---|
| | | Met | Lys | Gly | Ser | Ile | Pro | Arg | |

| CCC | TTT | ATT | GAT | GAT | TTG | CTG | ACA | AAG | TCC | GAT | ATT | 407 |
|---|---|---|---|---|---|---|---|---|---|---|---|---|
| Pro | Phe | Ile | Asp | Asp | Leu | Leu | Thr | Lys | Ser | Asp | Ile | |

| GTC | GAT | GTG | ATT | AAC | ACG | CGC | GTA | AAA | CTA | AAA | AAA | 443 |
|---|---|---|---|---|---|---|---|---|---|---|---|---|
| Val | Asp | Val | Ile | Asn | Thr | Arg | Vel | Lys | Leu | Lys | Lys | |

| GCT | GGC | CGC | GAT | TAT | CAA | GCC | TGC | TGC | CCT | TTC | CAT | 479 |
|---|---|---|---|---|---|---|---|---|---|---|---|---|
| Ala | Gly | Arg | Asp | Tyr | Gln | Ala | Cys | Cys | Pro | Phe | His | |

| CAC | GAA | AAA | ACA | CCA | TCC | TTC | ACA | GTT | AGC | CAA | AAG | 515 |
|---|---|---|---|---|---|---|---|---|---|---|---|---|
| His | Glu | Lys | Thr | Pro | Ser | Phe | Thr | Val | Ser | Gln | Lys | |

| AAA | CAG | TTT | TAT | CAC | TGC | TTT | GGC | TGC | GGC | GCG | | 548 |
|---|---|---|---|---|---|---|---|---|---|---|---|---|
| Lys | Gln | Phe | Tyr | His | Cys | Phe | Gly | Cys | Gly | Ala | | |

In addition to interrupting the MMS operon by binding to the mRNA transcribed from the operon, it is also possible to control other downstream products of the MMS operon to interrupt bacterial growth and to treat bacterial infections. For example, interrupting the function of the proteins encoded in the MMS operon also interrupts the function of the MMS operon and leads to death of the bacteria.

One embodiment of the present invention is a method for treating bacterial infections comprising the step of interrupting the function of proteins selected from the group consisting of S21, primase and sigma-70. This method comprises the step of competitively inhibiting a recognition site of a protein encoded by the MMS operon by introducing a competitive oligonucleotide into the bacteria.

The S21 recognition site includes the Shine-Dalagarno sequence located at the 3' end of the 16S rRNA and may be inhibited by introducing an oligonucleotide which competitively inhibits the binding of S21 in the bacteria. For example, an oligonucleotide of the sequence 5' GATCACCTCCTTA 3'.

The primase recognition site includes the phage G4 origin of replication site. Thus by introducing into bacteria a competitive oligonucleotide which interferes with this recognition site, bacterial growth and survival may be inhibited. An example of this competitive inhibitor is the loop III of the bacteriophage G4 $ori_c$ 5'GGCCGCCCCACATTGGGCAGGTATCTGAC-CAGTAGAGGGGCGGCC 3'.

The sigma-70 recognition site includes the core polymerase $\alpha_2\beta\beta'$ and this interaction confers specificity for promoter sequences. An example of this competitive inhibitor is 5'TTGACATAAATACCACTGGCGGT-GATACT 3'. This sequence is the bacteriophase lambda P_L promoter. This is the strongest promoter in E. coli and thus has the strongest known binding with RNA polymerase.

Thus the introduction of competitive oligonucleotides for these sequences into the bacteria will result in competitive interaction with the protein recognition site, thus preventing the binding of the S21, primase or sigma-70 molecules to the recognition site. This will interrupt normal cell function, growth and replication. Introduction of these oligonucleotides into the bacteria, disrupts the MMS operon's function and thus successfully treats bacterial infections.

The following examples are offered by way of illustration and are not intended to limit the invention in any manner.

EXAMPLE 1

The MMS Operon

Figure 12:
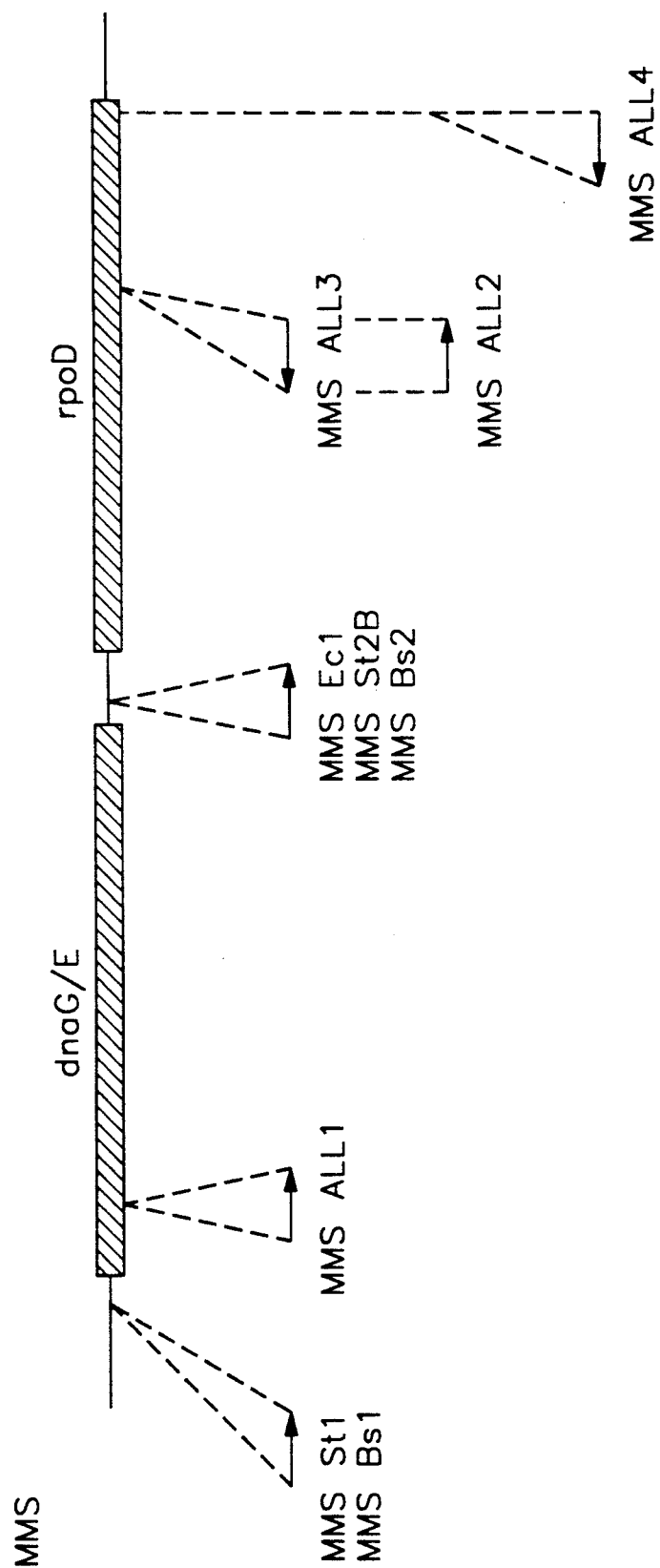
FIG. 12 is a schematic representation of PCR primers used to identify the intergenic sequences between the dnaG/E and rpoD genes in the macromolecular synthesis operon.
Figure 13:
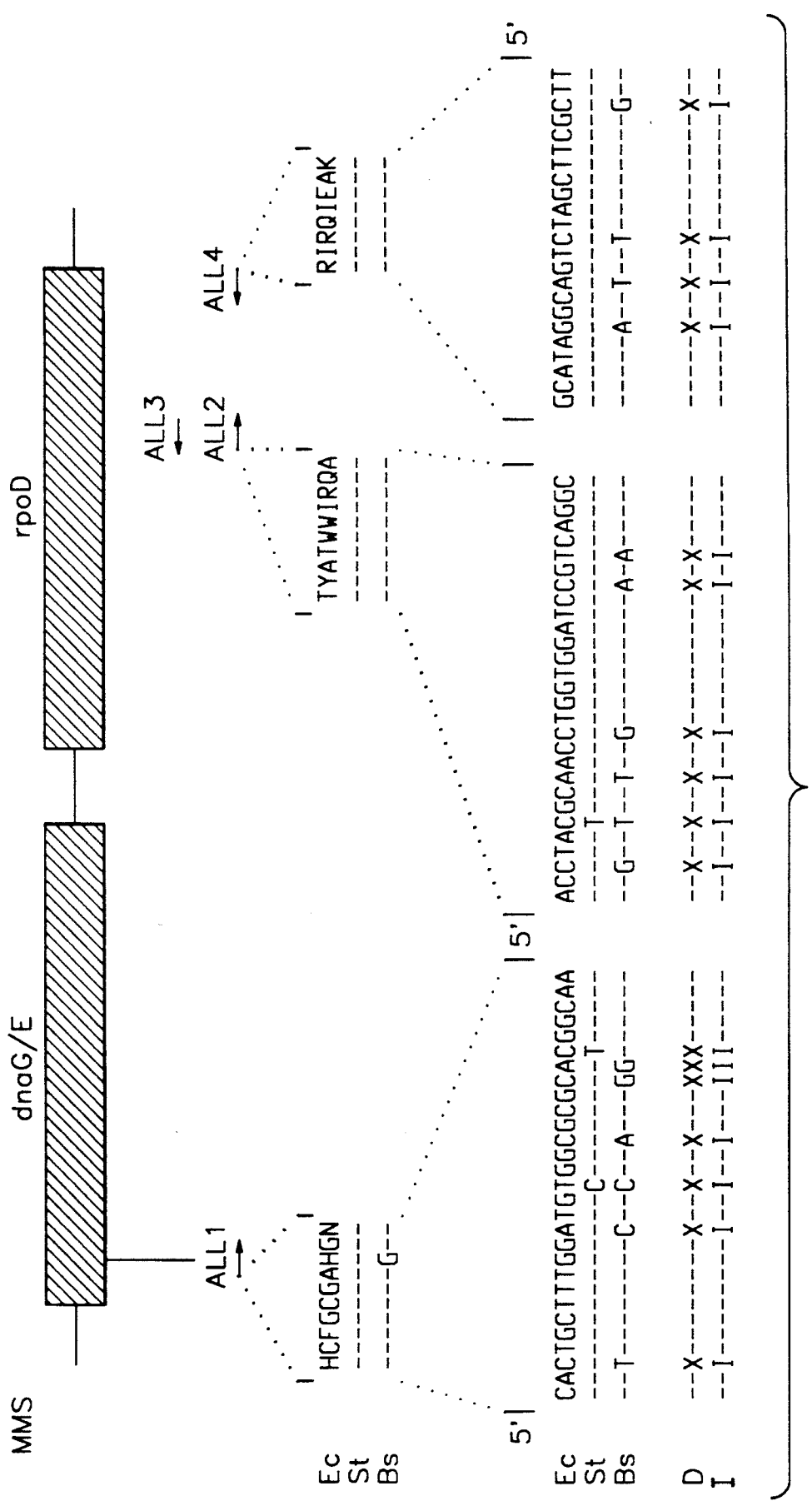
FIG. 13 is a schematic representation of the PCR amplification of the conserved macromolecular synthesis operon regions showing the actual sequence used in the primers. Ec refers to *E. coli* primer, St to the *S. typhimurium* primer, Bs to the *B. Subtilis* primer, D refers to the degenerate primer and I refers to the primer with inosine. Conserved homologous region primers were chosen from regions where the amino acid sequence was conserved between *E. coli, S. typhimurium* and *B. subtilis*.

The positions within the MMS operon of the primers used in the following examples are depicted in FIG. 12, and the sequences are shown in Tables 3 and 4. At the top of FIG. 12 is a schematic representation of a portion of the general schema for all MMS operons. The expressed sequences or genes dnaG and rpoD are depicted by hatched boxes. The conserved areas within the genes are depicted by arrows. Intergenic sequences are depicted by a single line between hatched boxes. The point of the arrow represents the 3' end of the individual primers. Nomenclature for actual DNA sequences of each primer is as follows: (1) MMS ALL—refers to primers or probes which recognize homologous regions of the MMS operons from all bacteria. They are based on conserved regions of the dnaG gene and rpoD gene in these organisms. MMS ALL#I refers to oligonucleotides where inosine is used to allow base pairing at nonconserved nucleotides while MMS ALL#D represents a degenerate oligonucleotide wherein any base is a possible replacement in the nonconserved position. The individual # refers to the position within the MMS operon. MMS Ec#, MMS St#, and MMS Bs# refers respectively to *Escherichia coli, Salmonella typhimurium* or *Bacillus subtilis* species specific identifier sequences from the MMS operon intergenic regions. The primers used can be: (1) primers with the actual sequence; (2) primers which contain inosine substitutions; and (3) combinations of degenerate primers.

Figure 2:
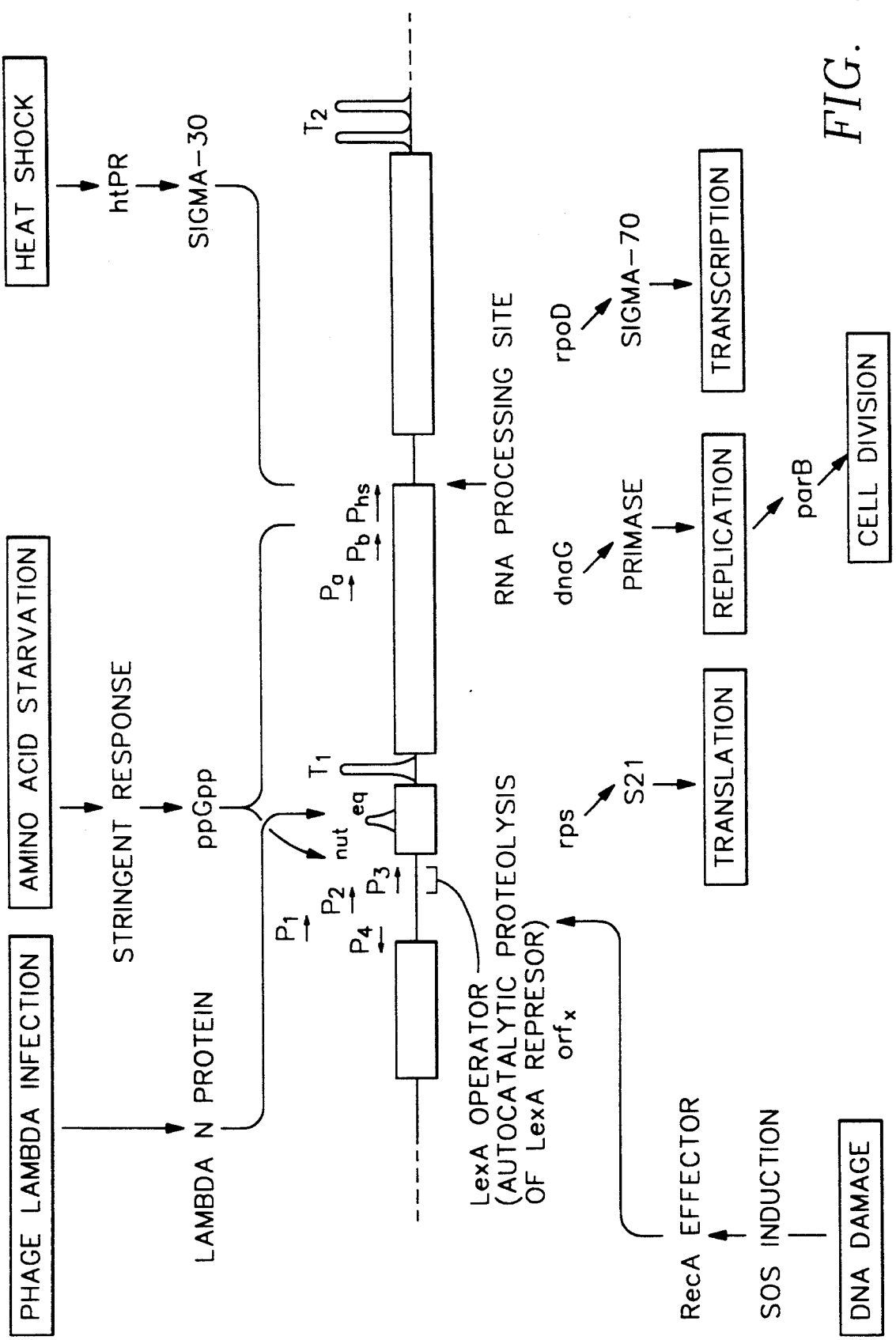
FIG. 2 depicts the regulation of the $E.$ $coli$ macromolecular synthesis operon. The three genes in the macromolecular synthesis operon are depicted as closed boxes. The cis-acting regulatory sequences include promoters ($P_x$, $P_1$, $P_2$, $P_3$, $P_a$, $P_b$, $P_{hs}$), terminators ($T_1$ and $T_2$), a LexA binding site, $nut_{eq}$ and an RNA processing site. The trans acting factors are shown with arrows drawn to where they are believed to act. The NusA protein increases rpoD gene expression, but its site of action is unknown. Global regulatory networks that interact with the macromolecular synthesis operon include the SOS, heat shock and stringent response. A functional role for $orf_x$ has not been assigned, but the proximity of $P_x$ and the conservation of the $orf_x$ sequences in $E.$ $coli$ and $S.$ $typhimurium$ suggests a possible macromolecular synthesis operon regulatory role. There are several other open reading frames further upstream with no assigned function and the nearest gene mapped on the *E. coli* chromosome is the cca gene which is 14 kb away.

In FIG. 2 and FIG. 3, the actual nucleotide sequences, or composition of matter, used in the experiments are shown.

EXAMPLE 2

Isolation of Unique Intergenic Sequences From the MMS Operon of L. monocytogenes The conserved homologous regions from the expressed genes within the MMS operon were used to obtain the nucleotide sequence of the unique intergenic species specific regions of the MMS operon. Oligonucleotide primers complementary to the conserved homologous region from the rpsU, dnaG and rpoD genes were made. Combinations of these primers were used in a polymerase chain reaction (PCR) on bacterial chromosomal DNA from diverse bacterial species. Almost all bacteria amplified a specific unique DNA fragment from DNA located in the MMS operon. This unique DNA sequence was located in the intergenic region between the primers and contains the unique intergenic sequence.

Figure 8A:
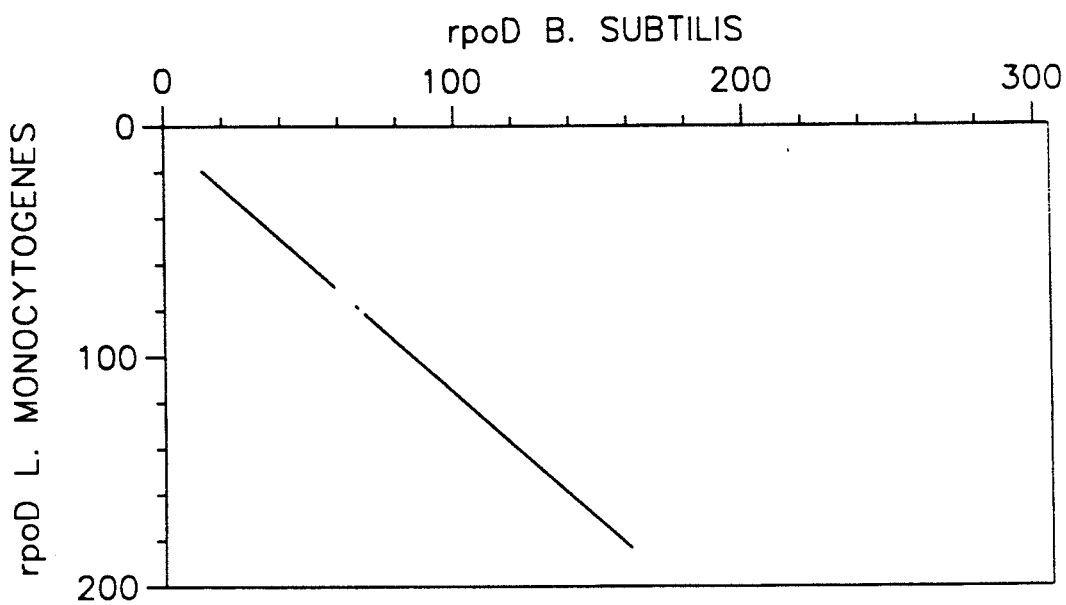
FIG. 8 (A)(B)(C) is a dot matrix plot of the *L. monocytogenes* rpoD amino terminus versus the known sigma factor genes in *B. subtilis, E. coli* and *S. Typhimurium*. The diagonal line represents homologous region shared by the expressed rpoD sequences of these organisms.
Figure 8B:
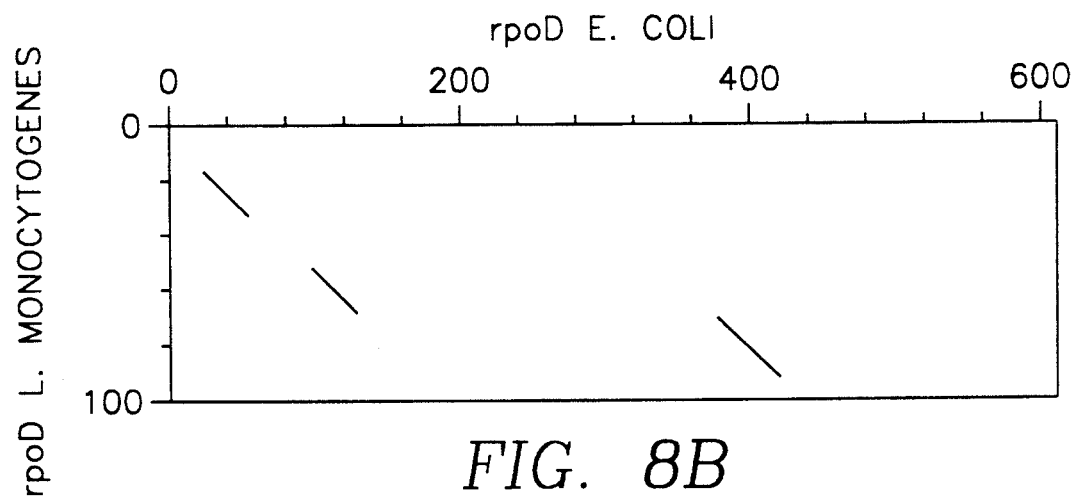
Figure 8C:
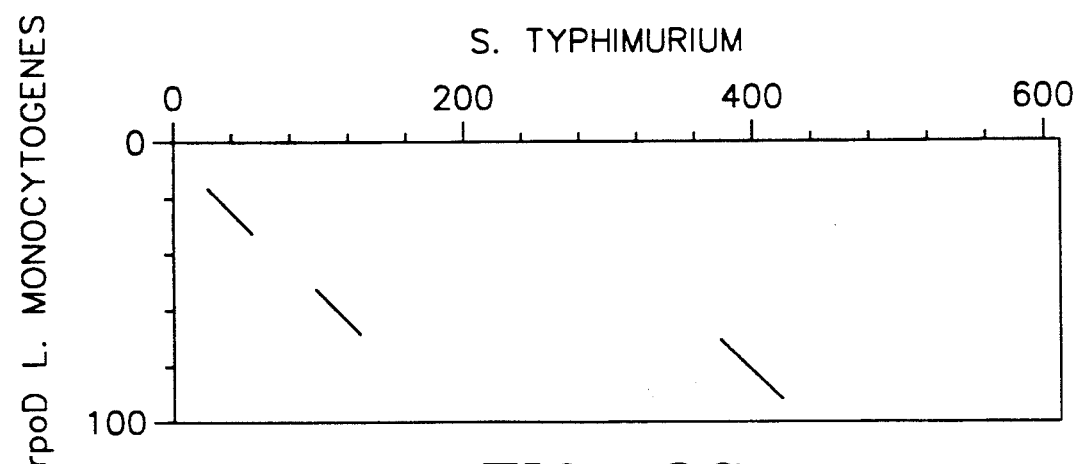
Figure 9A:
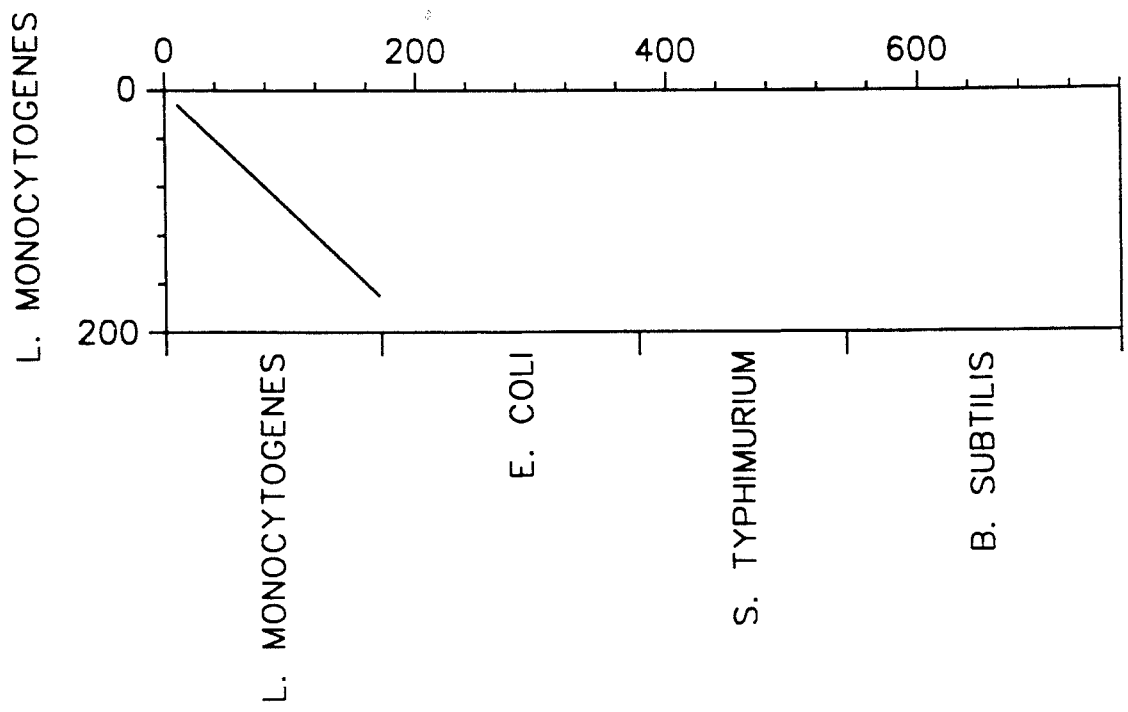
FIG. 9 (A)(B)(C)(D) is a dot matrix plot of the rpoD-dnaG intergenic sequence comparisons between *L. monocytogenes, E. coli, S. typhimurium* and *B. Subtilis*. This demonstrates the species specificity of the intergenic region.
Figure 9B:
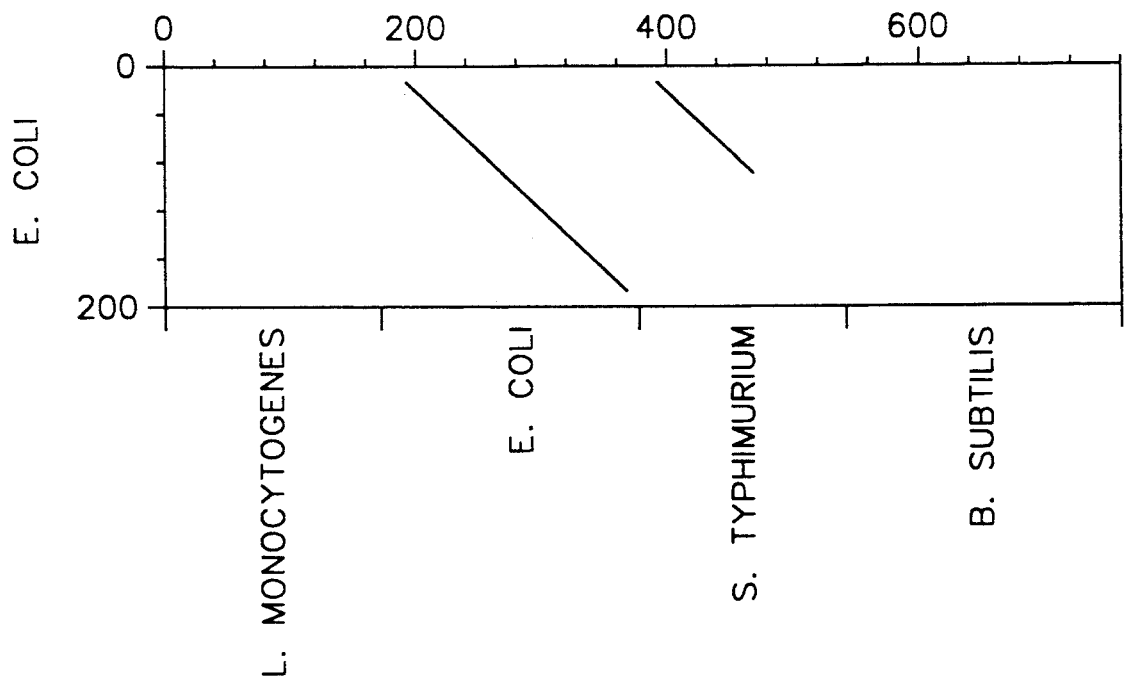
Figure 9C:
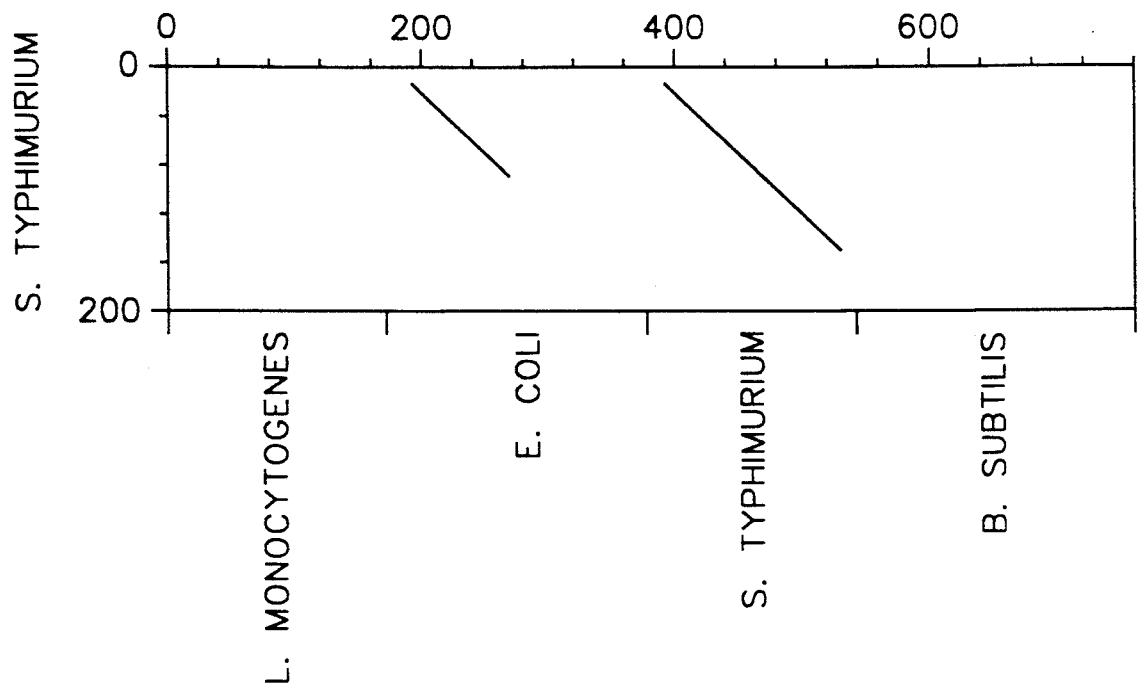
Figure 9D:
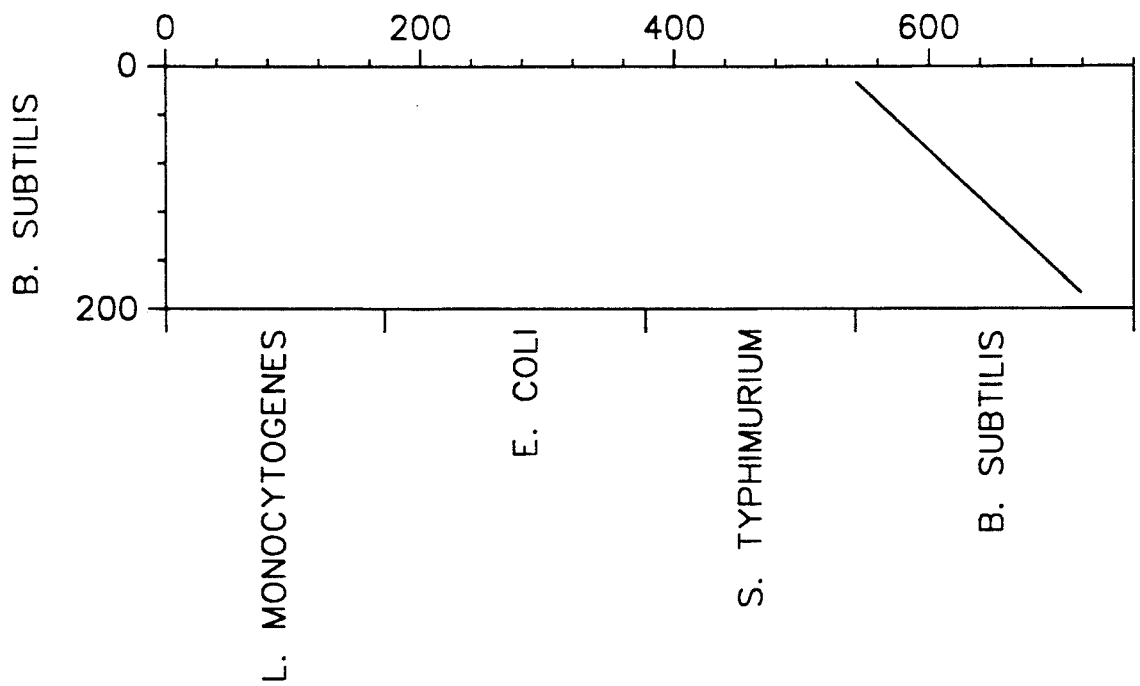
Figure 10A:
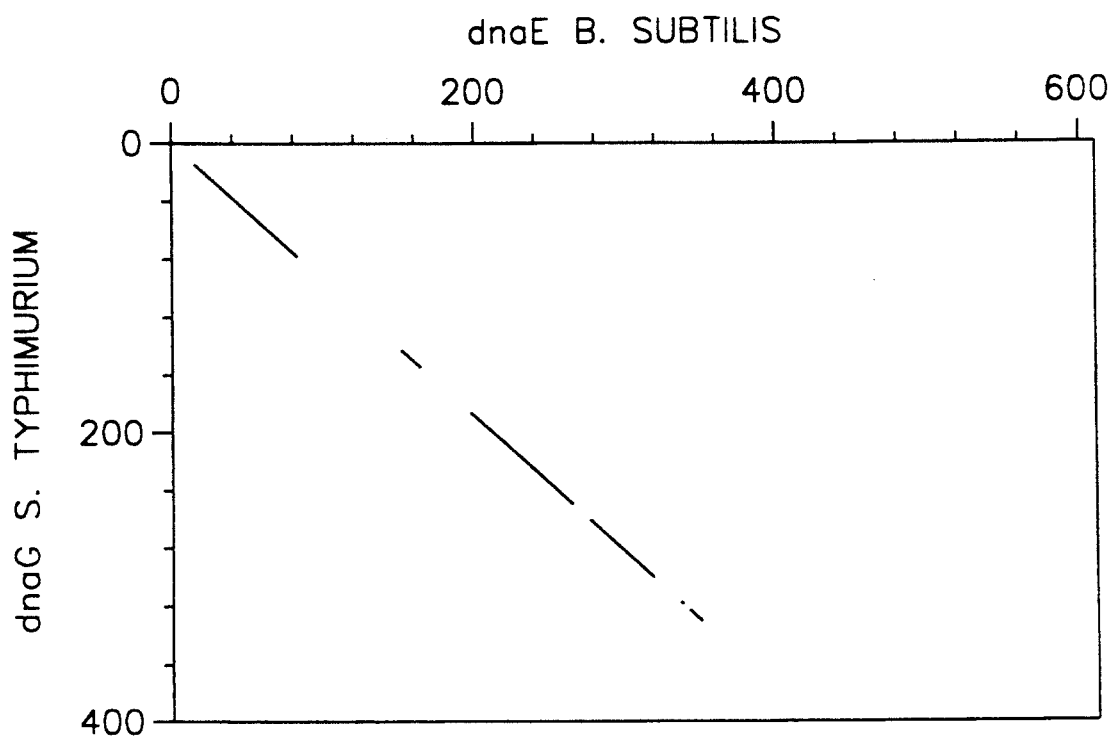
FIG. 10 (A)(B)(C)(D) is a dot matrix plot comparison of the dnaG/E primase genes of *B. subtilis, E. coli* and *S. typhimurium*.
Figure 10B:
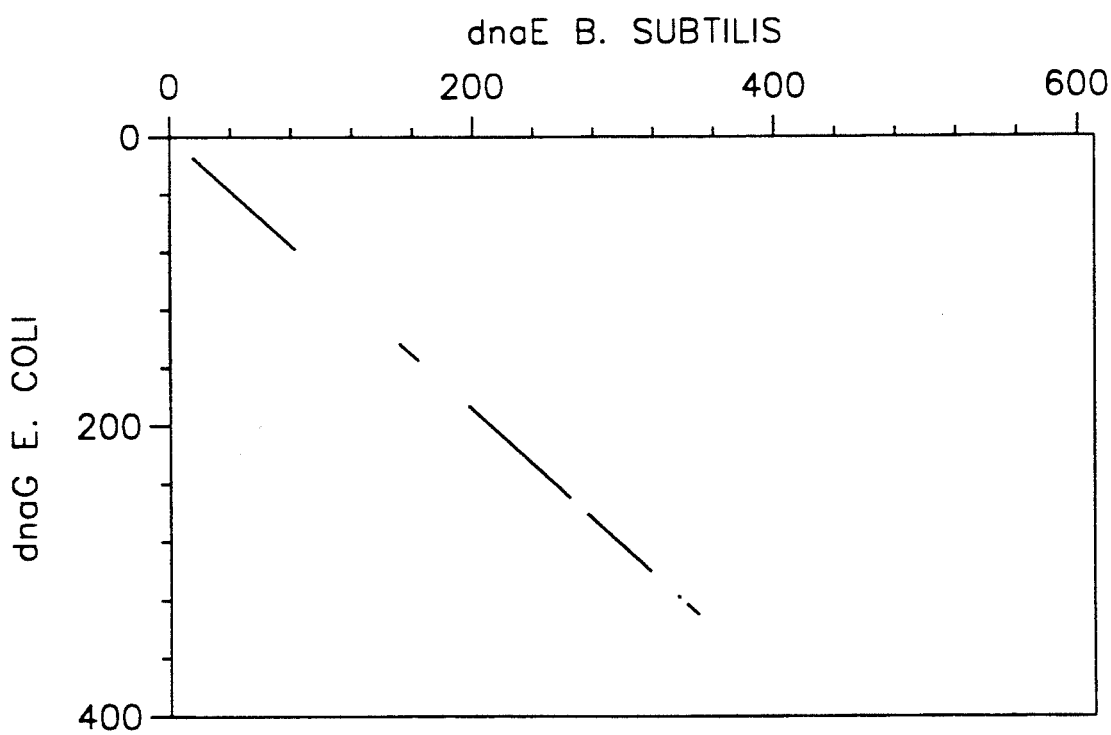
Figure 11A:
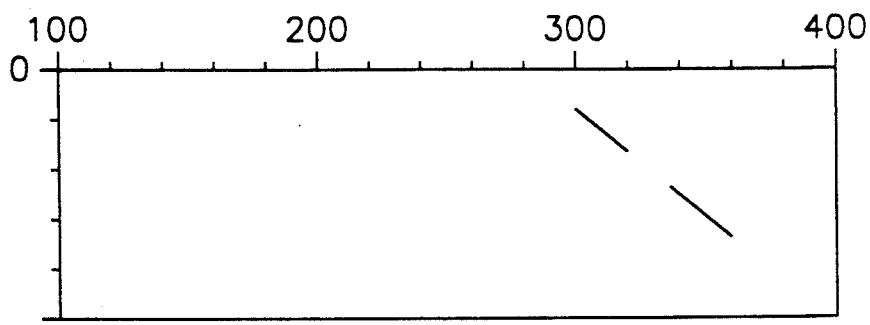
FIG. 11 (A)(B)(C) is a dot matrix plot of the *L. monocytogenes* dnaG internal segment versus the known primase genes of *S. typhimurium, E. coli,* and *B. subtilis*. This demonstrates conserved homologous regions in the dnaG gene of these organisms.
Figure 11B:
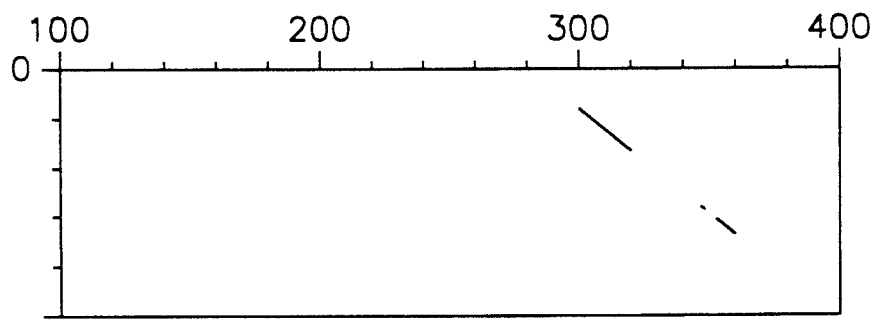
Figure 11C:
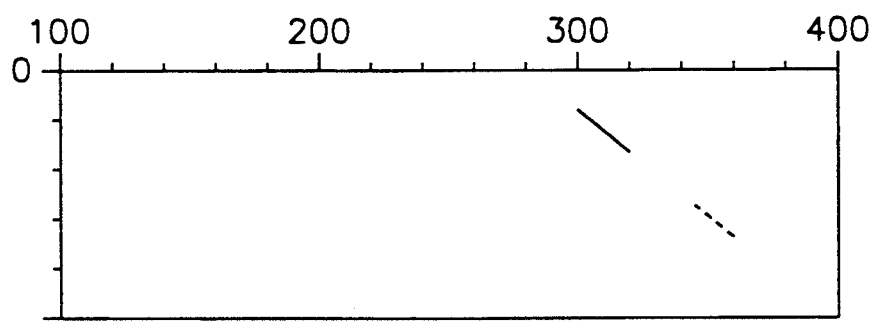

In *L. monocytogenes* the MMS operon DNA sequences were amplified using primers to the conserved homologous regions of dnaG and rpoD. The primer to the dnaG gene is 5' to 3' and complementary to the 3' to 5' strand, while the primer to the rpoD gene is 3' to 5' and complementary to the 5' to 3' strand. The PCR amplified fragment was sequenced to determine the entire DNA sequence. This sequence was compared with published sequences of the dnaG/E and rpoD genes from *E. coli, S. typhimurium* and *B. subtilis*. (FIGS. 8, 10 and 11). It was readily apparent that the PCR amplified sequence from *L. monocytogenes* correspond to the dnaG/E and rpoD expressed genes from other bacterial species. From comparing the sequences the dnaG and rpoD intergenic region for *L. monocytogenes* was deduced. (FIGS. 8, 9 and 11). The DNA sequence in this 197 bp *L. monocytogenes* dnaG and rpoD intergenic region is unique to the *Listeria* species. More importantly, computer analysis by dot plot matrix demonstrates that these *Listeria* dnaG-rpoD intergenic sequences do not share homology with the rpoD intergenic regions from *E. coli, S. typhimurium* or *B. subtilis*. (FIG. 9). This approach of using PCR amplification from the conserved homologous regions and computer comparisons of the amplified sequence by dot matrix plots with known MMS operon is a new and unique approach to isolating intergenic sequence. One skilled in the art will readily appreciate the applicability of this technique across a wide spectrum of bacteria.

EXAMPLE 3

Isolation of Unique Intergenic Sequence from the MMS Operon of H. influenzae In *H. influenzae* the conserved homologous regions from the expressed genes, rpsU and dnaG genes were used as primers to amplify the macromolecular synthesis operon rpsU-dnaG intergenic sequences from *H. influenzae*. The primer to the rpsU gene is 5' to 3' and complementary to the 3' to 5' strand while the primer to the dnaG gene is 3' to 5' and complementary to the 5' to 3' strand. The PCR amplified fragment was sequenced to determine the entire DNA sequence. The sequence was compared with the published sequences of the rpsU and dnaG/E genes from *E. coli, S. typhimurium* and *B. subtilis*. It was readily apparent from the analysis of the PCR amplified sequence from *H. influenzae*, which regions corresponded to the rpsU and dnaG/E expressed genes. This enabled the deduction of the rpsU-dnaG intergenic region for *H. influenzae*.

The data from *L. monocytogenes* and *H. influenzae* clearly show that oligonucleotides complementary to the conserved regions in the expressed sequences of the macromolecular synthesis operon can be used as primers in a PCR reaction with chromosomal genomic DNA from any bacterial species to identify unique intergenic sequences.

EXAMPLE 4

Conserved Sequences within the MMS operon

To show that the expressed sequences within the MMS operon, rpsU, dnaG, rpoD, contain conserved homologous DNA sequences, the following oligonucleotide which recognized conserved DNA sequences within the dnaG gene was synthesized: 5'-CATC-CAAAGCAGTGGTAAAACTGTTT-3'.

This oligonucleotide was end labeled and used as a probe in Southern blotting. DNA was isolated from 12 different pathogenic strains of Salmonella obtained from the body fluids of infected patients, digested with HindIII and run on a 1% agarose gel. This digested chromosomal DNA was probed with the end-labeled dnaG oligonucleotide AOAMMS.

Figure 7:
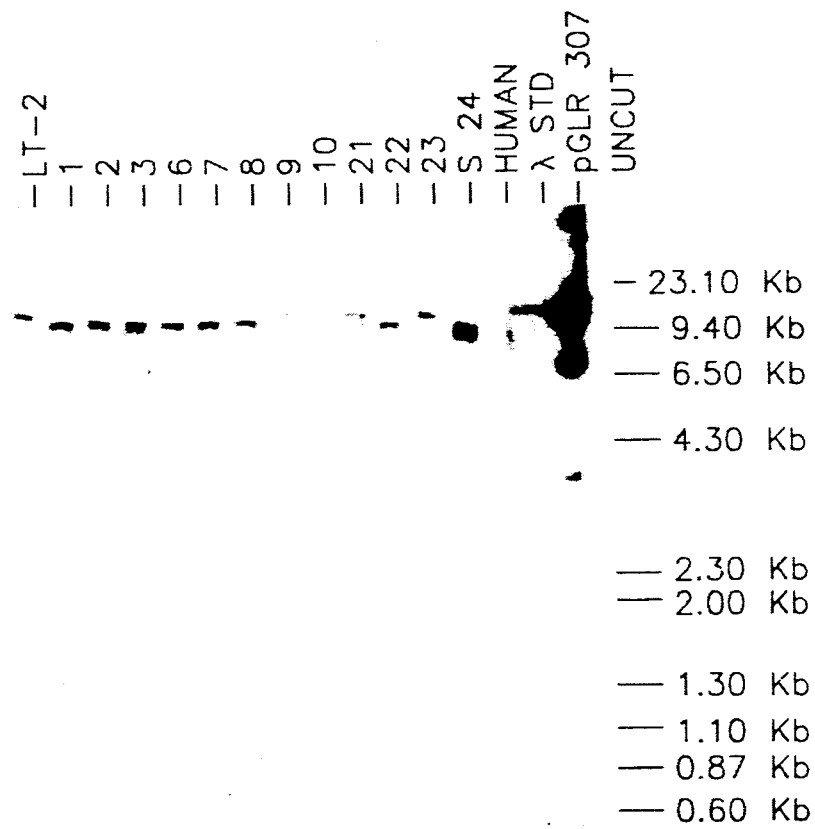
FIG. 7 is a picture of 1% agarose gel showing antisense binding of MMS operon probe sequences to restriction digested purified chromosomal DNA by Southern blotting.

As seen in FIG. 7, there is conservation of the oligonucleotide AOAMMS—dnaG in different pathogenic strains of Salmonella. The Southern blot shows homology of the oligonucleotide AOAMMS-dnaG to a laboratory control strain of Salmonella (LT-2) (lane 1) and twelve (12) different pathogenic strains isolated from body fluids of patients (lanes 2-13). There was no hybridization to human DNA (the negative control on lane 14), and as a positive control; a plasmid containing the DNA sequences in the probe showed a hybridization signal (lane 16). Lane 15 has lambda DNA cut with Hind III as a marker. On the far right are the sizes in kilobase pairs as determined on the agarose gel before Southern transfer.

EXAMPLE 5

Inhibition of Cell Growth

To inhibit cell growth, an inoculum of *E. coli* and *B. subtilis* are mixed in a single test tube and an antisense oligonucleotide to *E. coli* (AOAMMS-Eco) is added to the cell inoculum. The culture is gram stained after several hours of growth. Gram positive organisms are seen and there is a paucity of gram negative organisms. In a corollary experiment, an antisense oligonucleotide to *B. subtilis* (AOAMMS-Bsu) is added to a mixed inoculum of *E. coli* and *B. subtilis* and it is grown for several hours. On subsequent gram stain there is found negative rods. These experiments demonstrate species specific antisense oligonucleotide demise of bacterial organisms.

EXAMPLE 6

Hybridization of Probes

For the identification examples herein, a variety of methods can be used to identify bacteria using the unique intergenic sequence or the homologous sequence. For example: (1) the probe can be hybridized to the intergenic sequence directly as RNA or single stranded DNA in the bacteria; or (2) the unique intergenic sequence in the bacteria could be amplified by PCR and then the probe hybridized; or (3) the ligase chain reaction (LCR) can be run using special labeled probes. The hybridization can be detected by a variety of labels including: flourescence, chemiluminescense, enzymes, antibodies, radioisotopes or a combination of these.

For example, in the PCR assays described herein the conditions in Table 6 were used.

TABLE 6

| PRIMERS | STEP | PCR Conditions TEMPERATURE | TIME (Min) |
|---|---|---|---|
| Ec1,A113I | Initial | Denature | 94° | 9 |
| | Cycle | Denature | 90° | 30 |
| | Cycle | Anneal | 50°-60° | 1 |
| | Cycle | Extend | 65°-70° | 5-8 |
| St2B,A113I | Initial | Denature | 94° | 9 |
| | Cycle | Denature | 90° | 30 |
| | Cycle | Anneal | 50°-60° | 1 |

TABLE 6-continued

| PRIMERS | STEP | PCR Conditions TEMPERATURE | TIME (Min) |
|---|---|---|---|
| | Cycle | Extend | 70° | 5 |
| BsZ,A113I | Initial | Denature | 94° | 9 |
| | Cycle | Denature | 90° | 30 |
| | Cycle | Anneal | 60° | 1 |
| | Cycle | Extend | 70° | 5 |
| A112I,A113I | Initial | Denature | 94° | 9 |
| | Cycle | Denature | 90° | 30 |
| | Cycle | Anneal | 50°-55° | 1 |
| | Cycle | Extend | 65° | 8 |
| A112I,A114I | Initial | Denature | 94° | 9 |
| | Cycle | Denature | 90° | 30 |
| | Cycle | Anneal | 55° | 1 |
| | Cycle | Extend | 70° | 5 |

One skilled in the art readily appreciates that hybridization conditions are dependent on salt concentration and temperatures and readily knows how to adjust these to adjust the hybridization sensitivity.

EXAMPLE 7

MMS Operon Unique Intergenic Operon Identification by Use of Fluorescent Probes To directly identify a species of specific bacteria on a microscope slide the species specific intergenic sequences of the MMS operon was used. An oligonucleotide was synthesized complementary to the MMS operon intergenic sequence. This oligonucleotide is labeled with fluorescein on its 5' end by standard procedures. These fluorescent probes were placed on a microscope slide, the bacteria was fixed, the slide washed and the sample visualized by fluorescence microscopy. When the bacteria which contained the unique intergenic sequence was present fluorescence was seen.

EXAMPLE 8

Ligase Chain Reaction (LCR)

Another method of identification is the LCR method. In this method the 5' end of a probe is labeled with fluorescein and the 3' end is labeled with biotin. The unique intergenic sequence probe is split into two segments. The segments, one containing the fluorescein and one containing the biotin label, are added to the bacteria and LCR is run. The bacteria are identified after separation. Multiple bacteria can be simultaneously identified with this procedure if each species specific probe has a different fluorescent label.

EXAMPLE 9

Figure 14:
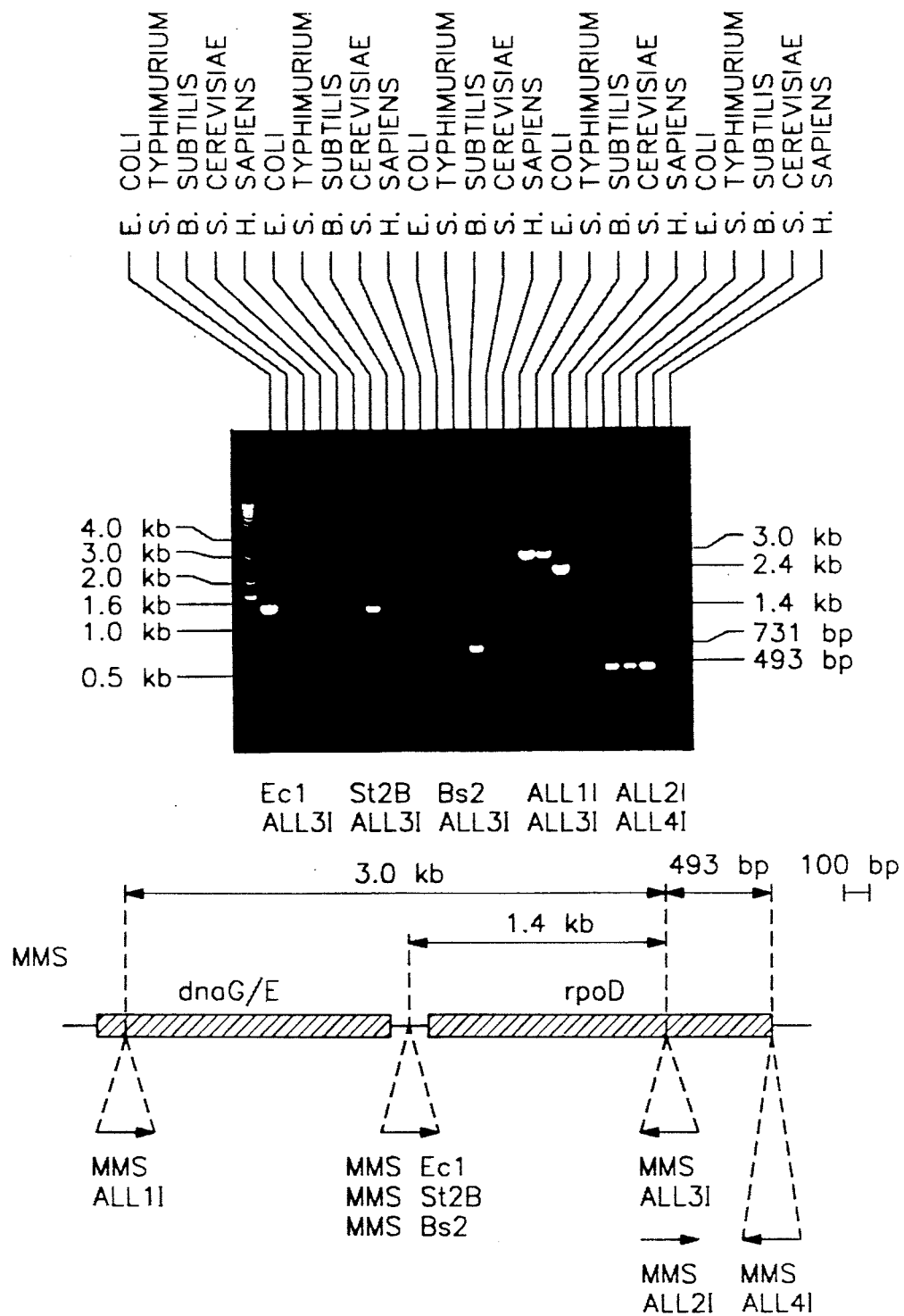
FIG. 14 is a schematic representation as well as a gel demonstrating the specificity of the macromolecular synthesis operon intergenic sequences.
Figure 15:
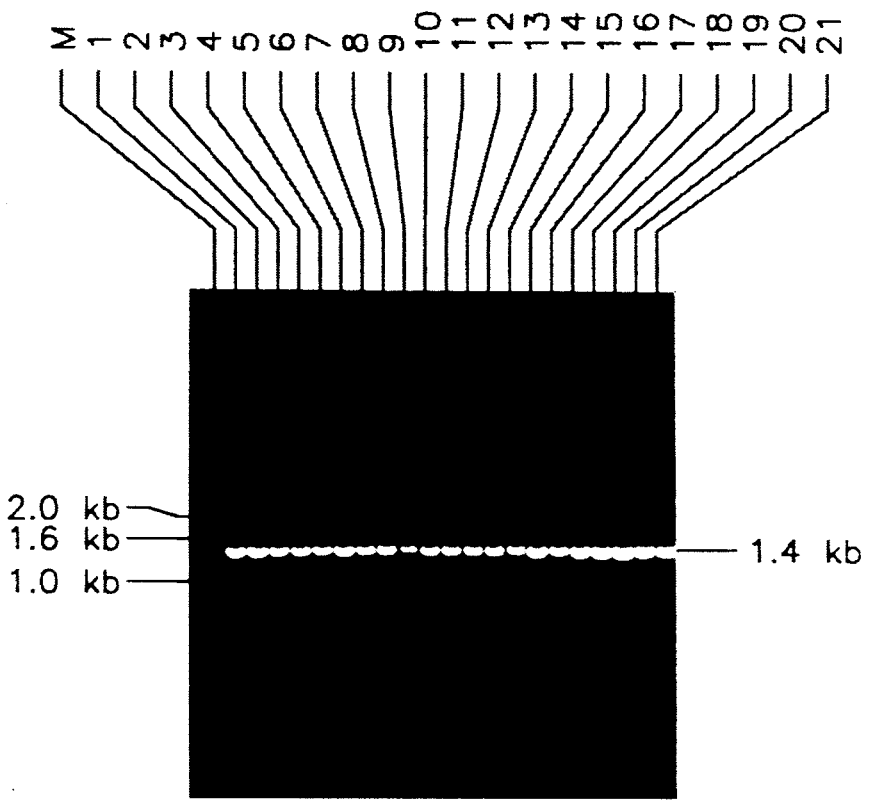
FIG. 15 is a gel showing that the unique intergenic oligonucleotide probe to the *E. coli* macromolecular synthesis operon intergenic regions recognizes all strains within an individual species of *E. coli*.
Figure 15:
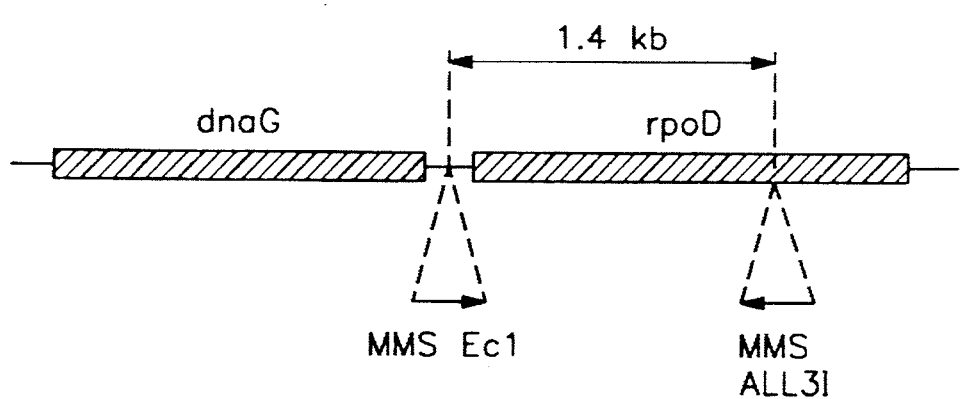

MMS Operon Intergenic Regions can be Utilized to Recognize All Strains Within an Individual Species FIG. 15 shows genomic DNA from 21 different strains of pathogenic *E. coli* isolated as specimens grown from bodily fluids of patients (cerebrospinal fluid, blood, urine, etc.). These specimens were used in a reaction with the *E. coli* species specific intergenic sequence primer MMS Ec1. As in FIG. 14, MMS ALL3I was used as the other primer in the standard PCR reaction. All the *E. coli* strains amplify the expected size fragment. The negative control, genomic DNA from *S. typhimurium*, did not amplify.

EXAMPLE 10

Specifics Specific Hybridization in S. typhimurium

Figure 16:
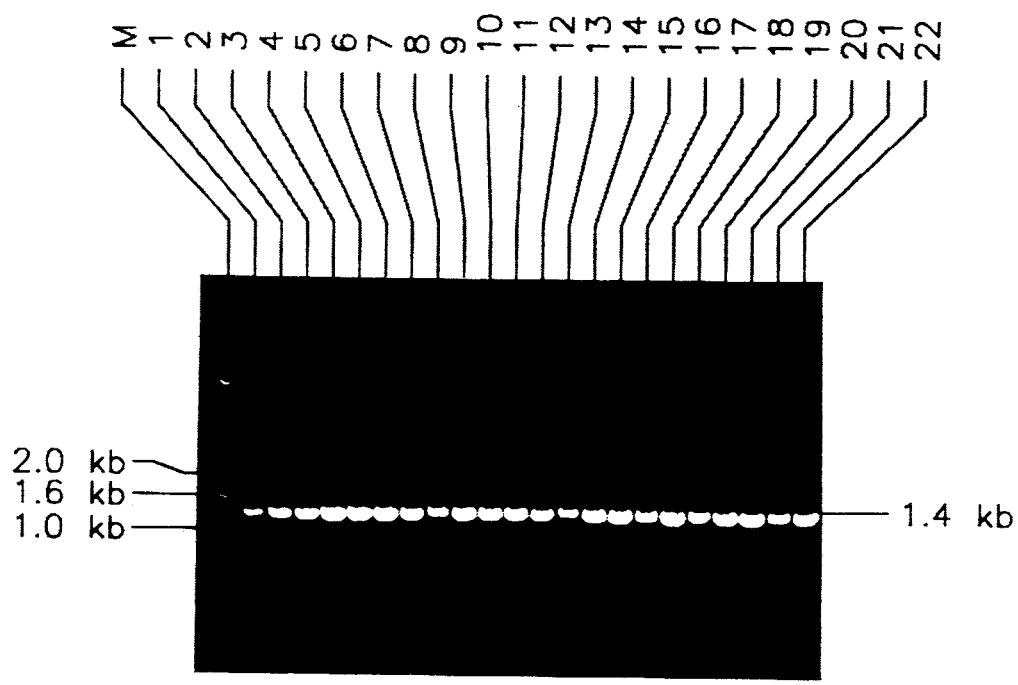
FIG. 16 is a gel showing a probe to the macromolecular synthesis operon intergenic regions can be utilized to recognize all strains within an individual species of *S. typhimurium*.
Figure 16:
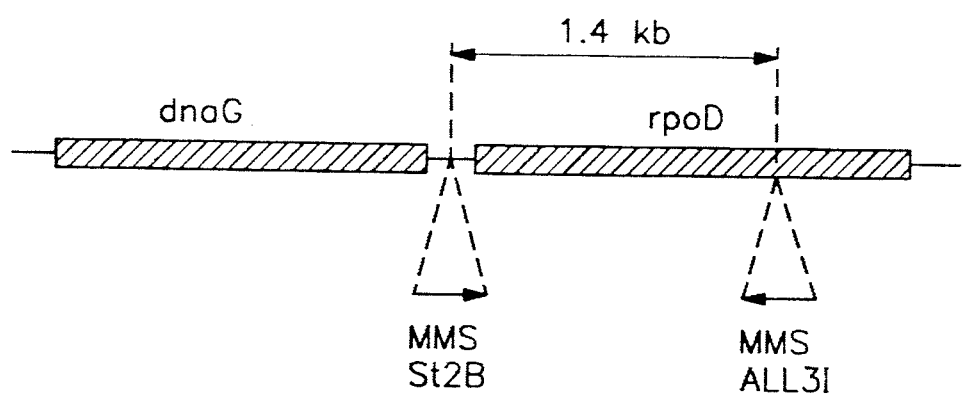

In FIG. 16, genomic DNA from 22 different strains of S. typhimurium were isolated from patient bodily fluids and were utilized. Note amplification of the expected size DNA fragment in all S. typhimurium strains when the species specific intergenic sequence primer was used.

EXAMPLE 11

Targeting Unique Intergenic Sequences from the MMS Operon to Detect Specific Bacterial Species The unique intergenic sequences from the macromolecular synthesis operon which can be obtained by a variety of procedures, including the novel methods described herein, can be used as targets for a DNA based probe diagnostic test to demonstrate the presence of a specific bacterial species in: (1) a clinical specimen (cerebrospinal fluid, urine, blood, etc.); (2) a food sample (chicken, oysters, infant formula, etc.); or (3) a water sample (ocean water, sewage system, city water supply, etc.). The presence of any bacteria is determined by virtue of the presence of homologous sequences from the MMS operon. The DNA from a particular bacterial species is determined by the presence of a unique intergenic species specific sequence from the macromolecular synthesis operon.

EXAMPLE 12

Figure 18:
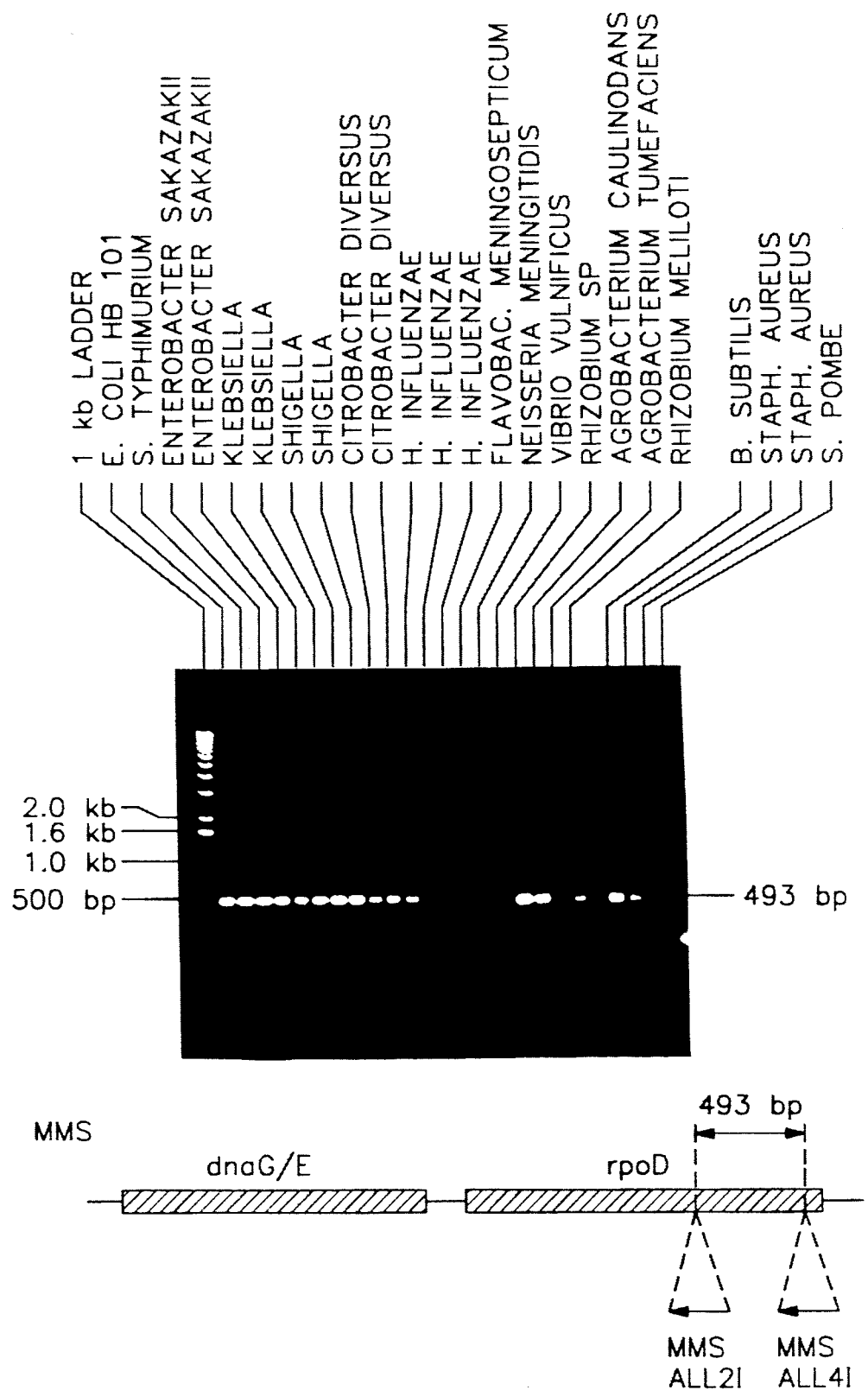
FIG. 18 is a gel showing the interspecies conservation of the rpoD homologous sequences.

Use of Conserved Homologous Regions from the MMS Operon to Detect the Presence of Bacteria Since the macromolecular synthesis operon is found in all bacterial species, and the expressed sequences or genes have conserved homologous regions, oligonucleotide probes can be designed from a consensus of the conserved homologous regions of several different bacterial species to enable the identification of any bacterial species. To make the consensus sequence all of the non-conserved bases are replaced with an inosene (I). Inosine will base pair by hydrogen bonding with any of the four usual bases A, C, G or T. Alternatively, multiple oligonucleotides can be synthesized with different bases at the non-conserved locations to yield a mixture of degenerate oligonucleotides. The degeneracy can be complete, placing all four possible bases (N=A, T, G and C) at a specific location or partial; placing less than four bases, based on deductions by examination of base sequences at the non-conserved position from a number of bacterial species. A mixture of the oligonucleotides can then be used to detect the presence of any bacteria. (FIG. 18). This is true because all bacteria have a macromolecular synthesis operon and all bacteria have conserved homologous regions within the expressed genes of the macromolecular synthesis operon. A probe that detects these conserved homologous regions therefore enables the detection of the presence of any bacteria.

EXAMPLE 13

Use of the Homologous Probe to Make a Clinical Diagnosis of Bacterial Meningitis Since it is very important to the physicians to be able to distinguish bacterial meningitis from viral meningitis, the homologous probe technique provides a very useful diagnostic test. This diagnostic test is based on the ability of the homologous probe to detect the presence of bacteria in a cerebrospinal fluid (CSF) specimen obtained after lumbar puncture. Normally, CSF fluid is sterile and thus does not contain any virus or bacteria. If bacteria are present in the CSF, the patient, by definition, has bacterial meningitis. Although this is life threatening, specific antibiotic treatment is available. Until the present invention, the standard procedure was to culture the CSF and wait 72 hours to see if any bacterial species grow.

The present invention uses either a consensus homologous sequence or a spinal fluid panel to test for bacterial meningitis. Since this test is quite efficient, quick and accurate, it is no longer necessary to wait 72 hours for bacteria to grow. The CSF is tested for bacteria by determining the presence of bacterial DNA. If bacterial DNA is present, then bacteria is present and thus, the patient has bacterial meningitis. The test can include a consensus sequence probe or a mixture of oligonucleotide probes to the conserved homologous regions from the expressed sequences of the macromolecular synthesis operon. The probes are used to detect the presence of any bacteria. An alternative embodiment of this invention is to use unique intergenic probes from the macromolecular synthesis operon. This allows the further identification of the bacteria. The unique intergenic probes can be used by themselves or in combination with the homologous probes to identify the bacteria. In one test panel the most commonly occurring bacterial pathogens for bacterial meningitis in the neonatal and pediatric age group, H. influenza, S. pneumoniae, N. meningitdus, grpB Streptococcus, L. monocytogenes and E. coli, are used to identify the specific bacterial species which is present in the CSF.

Figure 19:
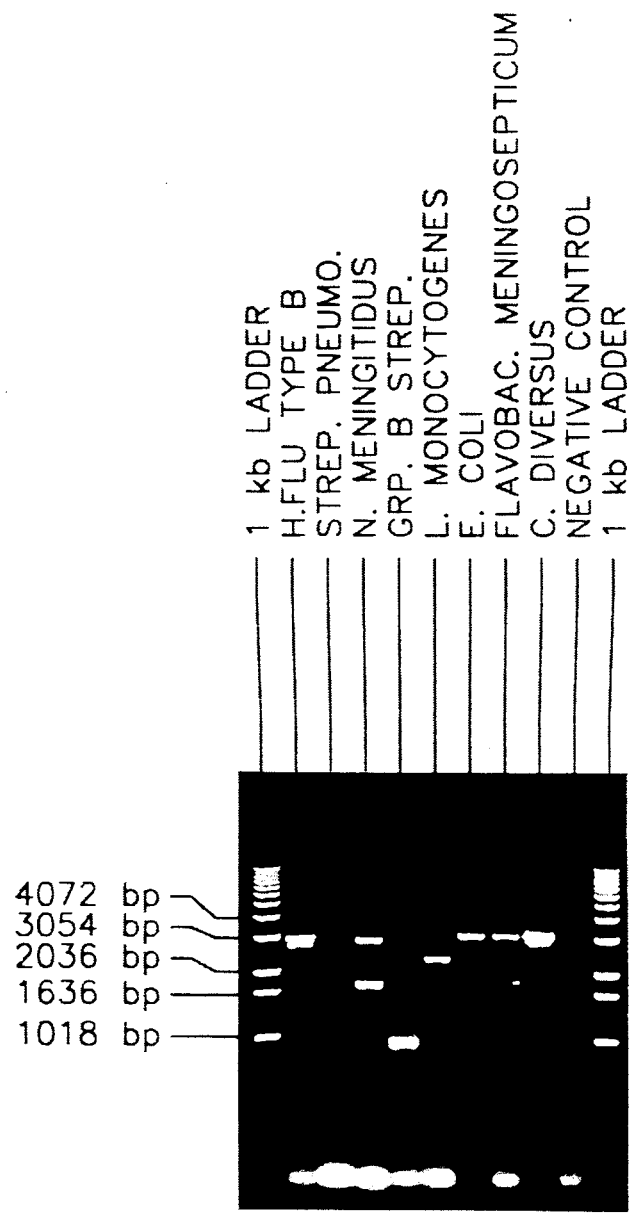
FIG. 19 is a gel showing the use of probes to the homologous sequence of dnaG and rpoD to isolate and identify the dnaG-rpoD intergenic sequences of various bacteria species.
Figure 19:
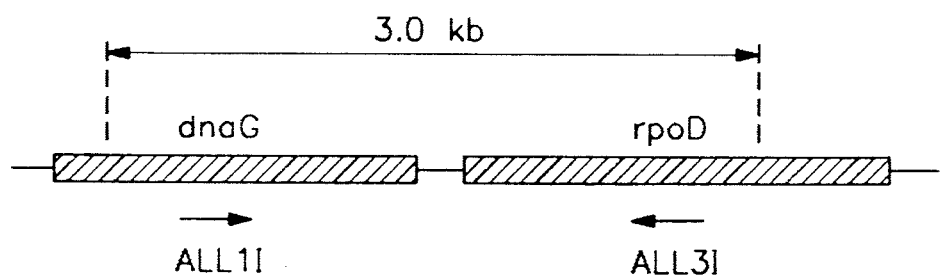
Figure 20:
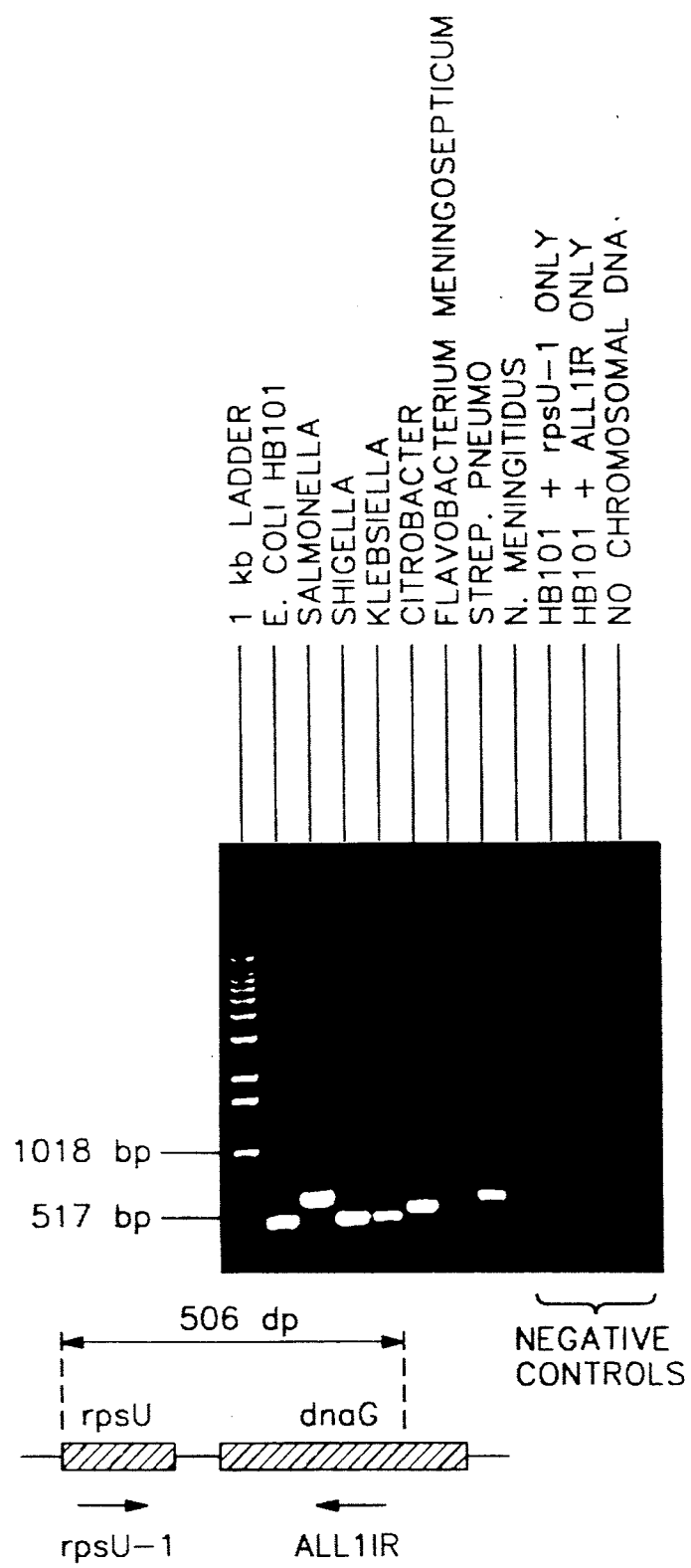
FIG. 20 is a gel showing the use of probe to the homologous sequences of rpsU and dnaG to isolate and identify rpsU-dnaG intergenic sequences in a variety of species.

FIGS. 19 and 20 show the rpsU-dnaG and dnaG-rpoD amplifications for organisms in the spinal fluid panel.

EXAMPLE 14

A Sexually Transmitted Disease (STD) Panel to Detect the Presence of Bacteria Associated with Sexually Transmitted Disease In the STD panel probes are made to the Unique Intergenic Region of bacteria associated with sexually transmitted disease. The initial bacteria used in the panel are: T. pallidum (the causative agent of syphylis), N. gonnorhea (the cause of gonnorhea) and Chlamydia species. The unique intergenic region from each of these bacteria are determined as outlined above for L. monocytogenes and H. influenzae.

Again, as in the case for the spinal fluid panel, the test includes oligonucleotide probes to the conserved homologous regions from the expressed sequences of the macromolecular synthesis operon to detect the presence of any bacteria. The probes for the MMS operon unique intergenic regions from T. palladium, N. gonnorhea and Chlamydia species are then used to test for the presence of these organisms.

EXAMPLE 15

Species Specificity of MMS Operon Intergenic Regions

FIG. 14 demonstrates species specificity of the MMS operon intergenic sequences. The species specific intergenic sequences MMS Ecl, MMS St2B, MMS Bs2 were utilized as primers in a PCR reaction with the rpoD gene homologous region probe MMS ALL3I used as the other primer. Standard reaction conditions were utilized for polymerase chain reaction (PCR). When MMS Ec1 is used only *E. coli* genomic DNA samples amplify the expected size fragment. The genomic DNA from *S. typhimurium* and *B. subtilis* does not amplify. Nor do yeast (*S. cerevisiae*) or human DNA (*H. sapiens*) negative controls.

It is further shown in FIG. 14 that when MMS St2B is used, only *S. typhimurium* genomic DNA amplifies the expected size fragment and when MMS Bs2 is used only *B. subtilis* genomic DNA amplifies the expected size DNA fragment. When homologous region probes are used as primers, MMS ALL1I plus MMS ALL3I, or MMS ALL2I plus MMS ALL4I, all three species, *E. coli*, *S. typhimurium* and *B. subtilis*, amplify the expected size fragment. Negative controls include human genomic DNA and yeast, *Sacharomyces cervisae* genomic DNA.

EXAMPLE 16

PCR Amplification of Conserved Homologous Regions

The MMS operon structure, and regions within expressed sequences or genes in the MMS operon, are conserved in all bacteria.

Figure 17:
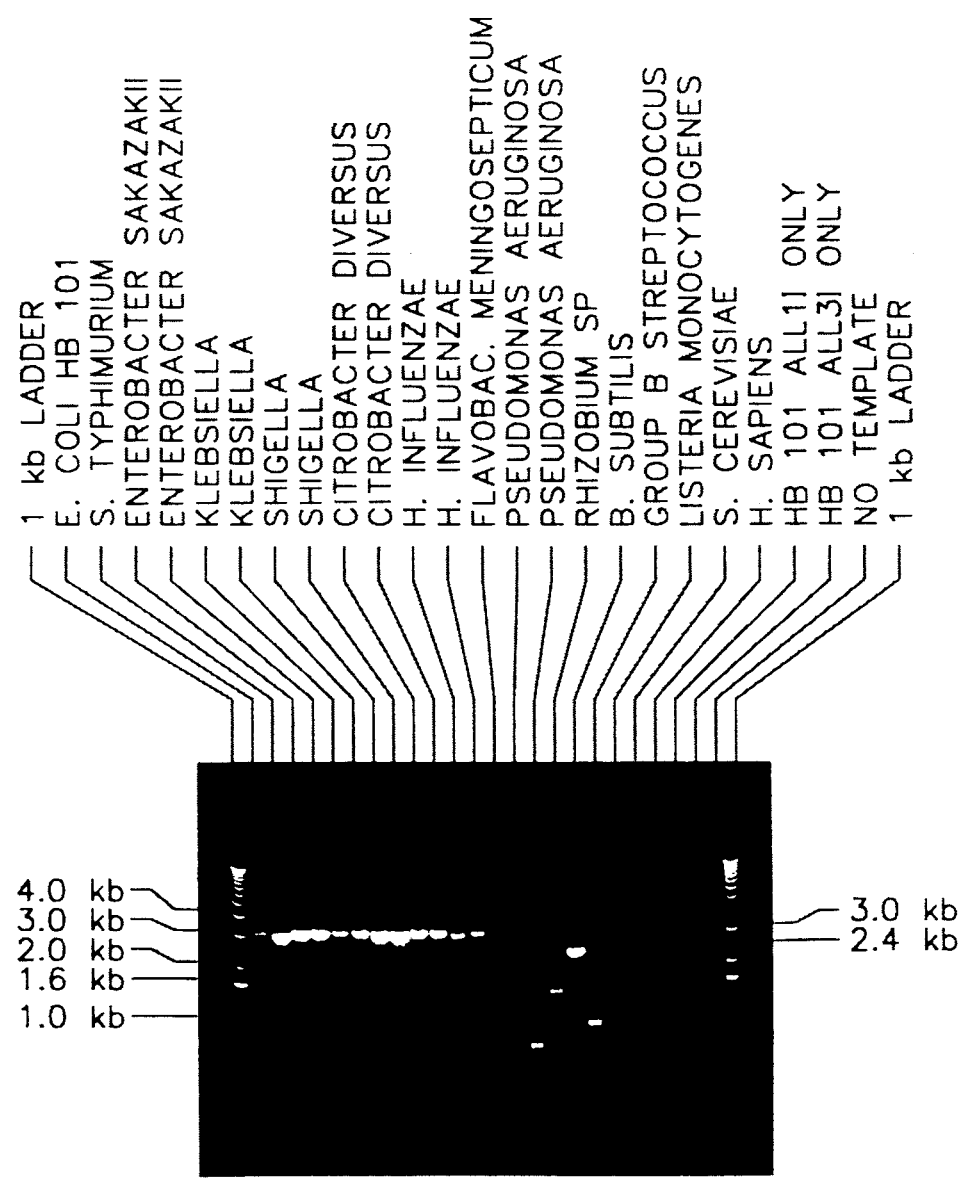
FIG. 17 is a gel showing interspecies conservation of the macromolecular synthesis operon sequences among a wide variety of bacterial species.
Figure 17:
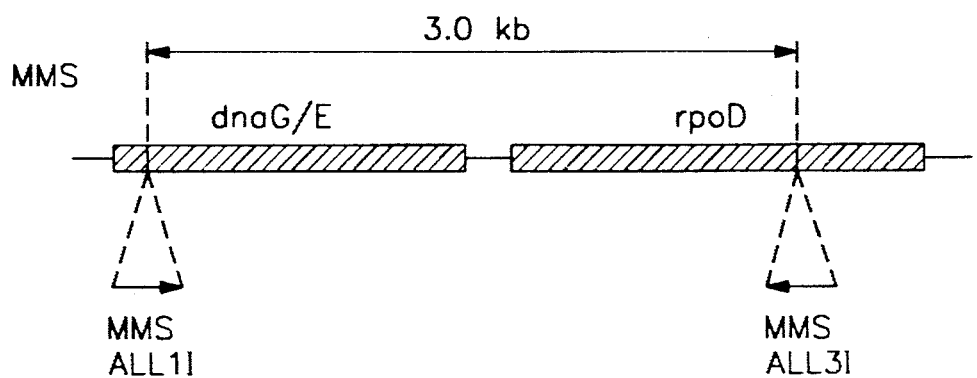

Oligonucleotide probes to homologous regions within the dnaG gene (MMS ALL1I) and the rpoD gene (MMS ALL3I) were used as primers in a PCR reactions with genomic DNA from various Eubacteria. PCR amplification of a specific size fragment will only take place if both (i) the homologous region probes are conserved in the dnaG and rpoD genes from these organisms and (ii) that the genes are contiguous or adjacent (thus confirming the MMS operon structure). In FIG. 17, every bacteria tested amplified a specific single DNA fragment. The different sizes of some species indicates that the homologous region of dnaG and rpoD genes are located at different distances apart. Thus, even though the sequence length was not conserved, the sequences still contained the homologous sequence. Negative controls, including human, yeast and the use of only one primer (either MMS ALL1I or MMS ALL-3I), and a reaction where no genomic DNA is placed in the reaction demonstrate no amplification.

These results demonstrate that: (1) the amplified DNA fragment must contain the unique intergenic region between dnaG and rpoD from these various microorganisms; (2) that the unique intergenic sequence be isolated and determined using the procedure of the present invention; (3) the intergenic regions of the MMS operon are species specific; (4) the MMS operon intergenic regions can be utilized to recognize all strains within an individual species (this is contrary to present day immunological methods which recognize surface antigens on a cell and do not recognize all strains within a species); (5) expressed sequences (genes) within the MMS operon are conserved in all bacteria and regions of homology within the dnaG gene and rpoD gene can be used to identify the presence of any bacteria by identifying these homologous regions within dnaG and rpoD; and (6) the macromolecular synthesis operon structure is conserved in all bacteria.

One skilled in the art will readily appreciate that the present invention is well adapted to carry out the objects and obtain the ends and advantages mentioned, as well as, those inherent therein. The oligonucleotides, antibiotics, compounds, methods, procedures and techniques described herein are presently representative of preferred embodiments, are intended to be exemplary, and are not intended as limitations on the scope. Changes therein and other uses will occur to those skilled in the art which are encompassed within the spirit of the invention or defined by the scope of the appended claims.

---

What is claimed is:

1. A method of identifying the presence or absence of a specific bacteria in a specimen, comprising the steps of:

hybridizing a unique intergenic antisense oligonucleotide of about 10 to 29 mer to a mRNA transcribed from a macromolecular synthesis (MMS) operon; and measuring the amount of said hybridization; wherein hybridization indicates the presence of said specific bacteria, and a lack of hybridization indicates said specific bacteria is not present, and wherein each unique intergenic antisense oligonucleotide only hybridizes to the mRNA transcribed from the MMS operon of a specific bacteria.

2. The method of claim 1, wherein the oligonucleotide is selected from the group consisting of:

5' GGCCCCGATTTTTAGCAA 3' and 5' TTATCGTTGGCGGTAAACAACCGTTGG 3'; and the bacteria is identified as E. coli.

3. The method of claim 1, wherein the oligonucleotide is selected from the group consisting of:

5' CTTGCGTAAGCGCCGGGG 3', 5' CGGCGCTTACGCAAGTCAGCGACA 3' and 5' CGACAGCTATACCGTCGACACC 3'; and the bacteria is identified as S. typhimurium.

4. The method of claim 1, wherein the oligonucleotide is selected from the group consisting of:

5' TATTCGATGCTTTAGTGC 3'; 5' GGGATTTGCACTAAAGCATCG 3' and 5' GATCGCTTAACCTCATCATG 3': and the bacteria is identified as B. subtilis.

5. The method of claim 1, wherein the oligonucleotide is 5' GTCGGTGTAGGAAGTTTTTCTAGGGCCG 3'; and the bacteria is identified as C trachomatis.

6. The method of claim 1, wherein the oligonucleotide is selected from the group consisting of 5' CCACGCGGATTGGGCGTAACGCTCTTGGG 3' and 5' CCCAAGAGCGTTACGCCCAATCCGCGTGG 3'; and the bacteria is identified as S. coelicolor.

7. The method of claim 1, wherein the oligonucleotide is 5' CGTGTCATGCTCGAAATCGTCCAACTC 3'; and the bacteria is identified as L. monocytogenes.

8. The method of claim 1, wherein the oligonucleotide is 5' CGCCCATGCAACCGGTTTGAGTTCGCG 3'; and the bacteria is identified as M xanthus.

9. A method of identifying the presence or absence of bacteria in a specimen, comprising the steps of:

hybridizing a homologous antisense oligonucleotide of about 10 to 29 mer to a mRNA transcribed from a macromolecular synthesis (MMS) operon; and measuring the amount of said hybridization, wherein hybridization indicates the presence of bacteria and a lack of hybridization indicates bacteria are not present, and wherein said homologous antisense oligonucleotide hybridizes to mRNA transcribed from the MMS operon of bacteria.

10. The method of claim 9, wherein the oligonucleotide is selected from the group consisting of 5' CATCCAAAGCAGTGGTAAAACTGTTT 3',
5' TCACCGATCGGCGTTTCCA 3',
5' CAITGCTTTGGITGIGGIGCGIIIGGCAA 3',
5' TTGCCIIICGCICCCICAICCAAAGCAITG 3',
5' CANTGCTTTGGNTGNGGNGCGNNNGGCAA 3',
5' TTGCCNNNCGCNCCNCANCCAAAGCANTG 3',
5' ACITAIGCIACITGGTGGATGIGICAGGC 3',
5' ACNTANGCNACNTGGTGGATCNGNCAGGC 3',
5' GCCTGICIGATCCACCAIGTIGCITAIGT 3',
5' GCCTGNCNGATCCACCANGTNGCNTANGT 3',
5' TTIGCTTCGATITGICGIATACG 3',
5' TTNGCTTCGATNTGNCGNATACG 3',
5' ACGAGCCGTTCGACGTAGCTCTGCG 3',
5' CGGCGTGCGTTTTCGCGAGCCAGT 3' and
5' GTAATTAAAGTACGTG 3'.

11. A method of identifying the presence or absence of a specific bacteria in a specimen, comprising the steps of:

treating a macromolecular synthesis (MMS) operon to form a single stranded DNA;

hybridizing an antisense oligonucleotide of about 10 to 29 mer to a unique intergenic sequence in the single stranded DNA of the operon; and measuring the amount of said hybridization; wherein hybridization indicates the presence of said specific bacteria, and a lack of hybridization indicates said specific bacteria is not present, and wherein each antisense oligonucleotide only hybridizes to the unique intergenic sequence of the MMS operon of said specific bacteria.

12. The method of claim 11, wherein the oligonucleotide is selected from the group consisting of 5' GGCCCCGATTTTTAGCAA 3' and 5' TTATCGTTGGCGGTAAACAACCGTTGG 3'; and the bacteria is identified as E. coli.

13. The method of claim 11, wherein the oligonucleotide is selected from the group consisting of 5' CTTGCGTAAGCGCCGGGG 3', 5' CGGCGCTTACGCAAGTCAGCGACA 3' and 5' CGACAGCTATACCGTCGACACC 3'; and the bacteria is identified as S. typhimurium.

14. The method of claim 11, wherein the oligonucleotide is selected from the group consisting of 5' TATTCGATGCTTTAGTGC 3', 5' GGGATTTGCACTAAAGCATCG 3' and 5' GATCGCTTAACCTCATCATG 3'; and the bacteria is identified as B. subtilis.

15. The method of claim 11, wherein the oligonucleotide is 5' GTCGGTGTAGGAAGTTTTTCTAGGGCCG 3'; and the bacteria is identified as C. trachomatis.

16. The method of claim 11, wherein the oligonucleotide is selected from the group consisting of 5' CCACGCGGATTGGGCGTAACGCTCTTGGG 3' and 5' CGTTACGCCCAATCCGCGTGG 3'; and the bacteria is identified as *S. coelicolor*.

17. The method of claim 11, wherein the oligonucleotide is 5' CGTGTCATGCTCGAAATCGTCCAACTC 3'; and the bacteria is identified as *L. monocytogenes*.

18. The method of claim 11, wherein the oligonucleotide is 5' CGCCCATGCAACCGGTTTGAGTTCGCG 3'; and the bacteria is identified as *M. xanthus*.

19. An assay for detecting the presence of bacteria in a sample selected from the group of clinical specimen, food specimen, and water specimen comprising:
   hybridizing a homologous antisense oligonucleotide of about 10 to 29 mer to a mRNA transcribed from a macromolecular synthesis (MMS) operon or single stranded bacterial DNA; and
   measuring the amount of said hybridization, wherein hybridization indicates the presence of bacteria, and a lack of hybridization indicates the absence of bacteria, and wherein said homologous antisense oligonucleotide hybridizes to the mRNA transcribed from the MMS operon or the single stranded DNA of the MMS operon region of bacteria.

20. The assay of claim 19, wherein said bacteria are identified by further hybridizing a unique intergenic antisense oligonucleotide of about 10 to 29 mer to said mRNA or single stranded DNA; wherein hybridization indicates the presence of a specific bacteria, and a lack of hybridization indicates said specific bacteria is not present, and wherein each unique intergenic sequence of the MMS operon of said specific bacteria, or to the mRNA transcribed therefrom.

21. An assay for detecting and identifying the presence of a specific bacteria in a sample selected from the group of clinical specimen, food specimen and water specimen comprising:
   hybridizing a unique intergenic antisense oligonucleotide of about 10-29 mer to a mRNA transcribed from a macromolecular synthesis (MMS) operon or single-stranded bacteria DNA; and measuring the amount of said hybridization, wherein hybridization indicates the presence of said specific bacteria, and a lack of hybridization indicates the absence of said specific bacteria, and wherein each unique intergenic antisense oligonucleotide only hybridizes to the unique intergenic sequence of the MMS operon of a specific bacteria.

22. The assay of either claim 20 or 21 for detecting bacterial meningitis, wherein the sample is CSF fluid; and
   the unique antisense oligonucleotide includes sequences selected from the MMS operon sequence of *H. influenzae, S. pneumoniae, N. meningitider*, group *B. Streptococcus L. monocytogenes* and *E. coli*.

23. The assay of either claim 20 or 21 for detecting bacteria causing sexually transmitted disease, wherein the unique antisense oligonucleotide includes sequences selected from the MMS operon sequences of *T. pallidum, N. gonnorhea* and *Clamydia* species.

24. The assay of either claim 20 or 21 for detecting bacteria causing food poisoning, wherein the unique antisense oligonucleotide includes sequences selected from the MMS operon sequences of *Lysteria, Vibrio cholera*, and *Salmonella*.

25. The assay of either claim 20 or 21 for detecting bacteria contaminated water, wherein the unique antisense oligonucleotide includes sequences selected from the MMS operon sequence of gram negative enteric bacteria.

* * * * *

UNITED STATES PATENT AND TRADEMARK OFFICE
CERTIFICATE OF CORRECTION

PATENT NO. : 5,294,533
DATED : March 15, 1994
INVENTOR(S) : James R. Lupski, et al.

It is certified that error appears in the above-indentified patent and that said Letters Patent is hereby corrected as shown below:

Column 2, line 30, change "$\alpha_2\beta\beta'''$" to -- $\alpha_2\beta\beta'$ --
Column 11, line 19, change "alogonucleotide" to -- oligonucleotide --
Column 14, line 10, after "unique" insert -- intergenic --
Column 14, Table 3, second row, last grouping, change "TCT" to -- TTC --
Column 17, Table 5, sixth row, fifth grouping, change "HCH" to -- GCG --
Column 20, line 24, change "rpoD" to -- dnaG-rpoD --
Column 24, line 55, change "*palladium*," to --pallidum--.
Column 25, line 24, change "ALLII" to --ALL1I--

Column 58, line 31, change "GTAATTAAAGTACGTG" to
    -- ACATGCCGGTAATTAAAGTACGTG --
Column 58, line 39, after "the" insert -- MMS --
Column 59, line 4, change "CGTTACGCCCAATCCGCGTGG" to
    -- CCCAAGAGCGTTACGCCCAATCCGCGTGG --
Column 59, line 36, after "intergenic" insert -- antisense oligonucleotide
    only hybridizes to the unique intergenic --

UNITED STATES PATENT AND TRADEMARK OFFICE
CERTIFICATE OF CORRECTION

PATENT NO. : 5,294,533
DATED : March 15, 1994
INVENTOR(S) : James R. Lupski, et al.

It is certified that error appears in the above-indentified patent and that said Letters Patent is hereby corrected as shown below:

Column 60, line 27, change "Clamydia" to --Chlamydia--.

Signed and Sealed this

Third Day of January, 1995

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 52

( 2 ) INFORMATION FOR SEQ ID NO: 1

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( i x ) FEATURE:

All X's in sequence represent inosine ( x i ) SEQUENCE DESCRIPTION: SEQ ID NO: 1

CAXTGCTTTG    GXTGXGGXGC    GXXXGGCAA    29

( 3 ) INFORMATION FOR SEQ ID NO: 2

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( i x ) FEATURE:

All X's in sequence represent inosine ( x i ) SEQUENCE DESCRIPTION: SEQ ID NO: 2

TTGCCXXXCG    CXCCXCAXCC    AAAGCAXTG          29

( 4 ) INFORMATION FOR SEQ ID NO: 3

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 3

CANTGCTTTG    GNTGNGGNGC    GNNNGGCAA          29

( 5 ) INFORMATION FOR SEQ ID NO: 4

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 4

TTGCCNNNCG    CNCCNCANCC    AAAGCANTG          29

( 6 ) INFORMATION FOR SEQ ID NO: 5

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( i x ) FEATURE:

All X's in sequence represent inosine ( x i ) SEQUENCE DESCRIPTION: SEQ ID NO: 5

ACXTAXGCXA    CXTGGTGGAT    GXGXCAGGC          29

( 7 ) INFORMATION FOR SEQ ID NO: 6

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 6

ACNTANGCNA    CNTGGTGGAT    CNGNCAGGC          29

( 8 ) INFORMATION FOR SEQ ID NO: 7

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( i x ) FEATURE:

All X's in sequence represent inosine ( x i ) SEQUENCE DESCRIPTION: SEQ ID NO: 7

GCCTGXCXGA    TCCACCAXGT    XGCXTAXGT             29

( 9 ) INFORMATION FOR SEQ ID NO: 8

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 8

GCCTGNCNGA    TCCACCANGT    NGCNTANGT             29

( 1 0 ) INFORMATION FOR SEQ ID NO: 9

( i ) SEQUENCE CHARACTERISTICS:
        ( A ) LENGTH: 23
        ( B ) TYPE: Nucleic acid
        ( C ) STRANDEDNESS: Single
        ( D ) TOPOLOGY: Linear ( i i ) MOLECULE TYPE: Genomic DNA ( i x ) FEATURE:

All X's in sequence represent inosine ( x i ) SEQUENCE DESCRIPTION: SEQ ID NO: 9

TTXGCTTCGA    TXTGXCGXAT    ACG                    23

( 1 1 ) INFORMATION FOR SEQ ID NO: 10

( i ) SEQUENCE CHARACTERISTICS:
        ( A ) LENGTH: 23
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 10

TTNGCTTCGA    TNTGNCGNAT    ACG                    23

( 1 2 ) INFORMATION FOR SEQ ID NO: 11

( i ) SEQUENCE CHARACTERISTICS:
        ( A ) LENGTH: 25
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 11

ACGAGCCGTT    CGACGTAGCT    CTGCG                25

( 1 3 ) INFORMATION FOR SEQ ID NO: 12

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 12

CGGCGTGCGT    TTTCGCGAGC    CAGT                        24

( 1 4 ) INFORMATION FOR SEQ ID NO: 13

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 13

ACATGCCGGT    AATTAAAGTA    CGTG                        24

( 1 5 ) INFORMATION FOR SEQ ID NO: 14

( i ) SEQUENCE CHARACTERISTICS:
        ( A ) LENGTH: 26
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 14

CATCCAAAGC    AGTGGTAAAA    CTGTTT                     26

( 1 6 ) INFORMATION FOR SEQ ID NO: 15

( i ) SEQUENCE CHARACTERISTICS:
        ( A ) LENGTH: 19
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 15

TCACCGATCG    GCGTTTCCA                            19

( 1 7 ) INFORMATION FOR SEQ ID NO: 16

( i ) SEQUENCE CHARACTERISTICS:
        ( A ) LENGTH: 18
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 16

GGCCCCGATT    TTTAGCAA                             18

( 1 8 ) INFORMATION FOR SEQ ID NO: 17

( i ) SEQUENCE CHARACTERISTICS:
        ( A ) LENGTH: 18
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 17

CTTGCGTAAG    CGCCGGGG                             18

( 1 9 ) INFORMATION FOR SEQ ID NO: 18

( i ) SEQUENCE CHARACTERISTICS:
  ( A ) LENGTH: 18
  ( B ) TYPE: Nucleic acid
  ( C ) STRANDEDNESS: Single
  ( D ) TOPOLOGY: Linear ( i i ) MOLECULE TYPE: Genomic DNA ( x i ) SEQUENCE DESCRIPTION: SEQ ID NO: 18

TATTCGATGC TTTAGTGC                                                     1 8

( 2 0 ) INFORMATION FOR SEQ ID NO: 19

( i ) SEQUENCE CHARACTERISTICS:
    ( A ) LENGTH: 21
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 19

GGGATTTGCA CTAAAGCATC G                                             2 1

( 2 1 ) INFORMATION FOR SEQ ID NO: 20

( i ) SEQUENCE CHARACTERISTICS:
    ( A ) LENGTH: 20
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 20

GATCGCTTAA CCTCATCATG                                               2 0

( 2 2 ) INFORMATION FOR SEQ ID NO: 21

( i ) SEQUENCE CHARACTERISTICS:
    ( A ) LENGTH: 28
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 21

GTCGGTGTAG GAAGTTTTC TAGGGCCG                                       2 8

( 2 3 ) INFORMATION FOR SEQ ID NO: 22

( i ) SEQUENCE CHARACTERISTICS:
    ( A ) LENGTH: 27
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 22

TTATCGTTGG CGGTAAACAA CCGTTGG                                       2 7

( 2 4 ) INFORMATION FOR SEQ ID NO: 23

( i ) SEQUENCE CHARACTERISTICS:
    ( A ) LENGTH: 18
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 23

GGCCCCGATT   TTTAGCAA                                    18

( 2 5 ) INFORMATION FOR SEQ ID NO: 24

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 24

CCACGCGGAT   TGGGCGTAAC   GCTCTTGGG              29

( 2 6 ) INFORMATION FOR SEQ ID NO: 25

( i ) SEQUENCE CHARACTERISTICS:
        ( A ) LENGTH: 29
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 25

CCCAAGAGCG   TTACGCCCAA   TCCGCGTGG              29

( 2 7 ) INFORMATION FOR SEQ ID NO: 26

( i ) SEQUENCE CHARACTERISTICS:
        ( A ) LENGTH: 27
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 26

CGCCCATGCA   ACCGGTTTGA   GTTCGCG                 27

( 2 8 ) INFORMATION FOR SEQ ID NO: 27

( i ) SEQUENCE CHARACTERISTICS:
        ( A ) LENGTH: 27
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 27

CGCCCATGCA   ACCGGTTTGA   GTTCGCG                 27

( 2 9 ) INFORMATION FOR SEQ ID NO: 28

( i ) SEQUENCE CHARACTERISTICS:
        ( A ) LENGTH: 24
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 28

CGGCGCTTAC   GCAAGTCAGC   GACA                     24

( 3 0 ) INFORMATION FOR SEQ ID NO: 29

(i) SEQUENCE CHARACTERISTICS:
    (A) LENGTH: 22
    (B) TYPE: Nucleic acid
    (C) STRANDEDNESS: Single
    (D) TOPOLOGY: Linear (ii) MOLECULE TYPE: Genomic DNA (xi) SEQUENCE DESCRIPTION: SEQ ID NO: 29

| CGACAGCTAT | ACCGTCGACA | CC | | 22 |
|---|---|---|---|---|

(31) INFORMATION FOR SEQ ID NO: 30

(i) SEQUENCE CHARACTERISTICS:
    (A) LENGTH: 1043
    (B) TYPE: Nucleic acid
    (C) STRANDEDNESS: Single
    (D) TOPOLOGY: Linear (ii) MOLECULE TYPE: Genomic DNA (xi) SEQUENCE DESCRIPTION: SEQ ID NO: 30

| GCA | ACT | TCT | TGG | TGC | AAC | ATC | GTT | TAT | 27 |
|---|---|---|---|---|---|---|---|---|---|
| Ala | Thr | Ser | Trp | Cys<br>5 | Asn | Ile | Val | Tyr | |
| CAT | GAT | AAT | TAC | AAA | GCG | CTT | TAT | ACC | 54 |
| His<br>10 | Asp | Asn | Tyr | Lys<br>15 | Ala | Leu | Tyr | Thr | |
| TAT | CTA | ATT | GGT | TAT | TTC | TGG | CAG | AAG | 81 |
| Tyr | Leu<br>20 | Ile | Gly | Tyr | Phe | Trp<br>25 | Gln | Lys | |
| GTA | ATG | ATG | CAG | ATC | CAA | CGG | AAA | TTT | 108 |
| Val | Met | Met<br>30 | Gln | Ile | Gln | Arg | Lys<br>35 | Phe | |
| ATG | GAT | AGT | GTT | CCT | GAT | GCT | ACA | ATG | 135 |
| Met | Asp | Ser | Val<br>40 | Pro | Asp | Ala | Thr | Met<br>45 | |
| AAA | GGA | CTT | ATC | AGT | AGC | CTC | GAA | ATG | 162 |
| Lys | Gly | Leu | Ile | Ser<br>50 | Ser | Leu | Glu | Met | |
| GTT | ATT | AGT | CCA | GAT | GAA | CAA | GGT | AAA | 189 |
| Val<br>55 | Ile | Ser | Pro | Asp | Glu<br>60 | Gln | Gly | Lys | |
| ACA | CAG | TTT | GAA | GAC | TAT | ATT | AGA | AGT | 216 |
| Thr | Gln<br>65 | Phe | Glu | Asp | Tyr | Ile<br>70 | Arg | Ser | |
| CTA | AAG | CGG | TTT | AAA | TTA | GAA | CAA | AAG | 243 |
| Leu | Lys | Arg<br>75 | Phe | Lys | Leu | Glu | Gln<br>80 | Lys | |
| AAA | AAA | GAA | CTT | GAG | CAA | GAG | CTA | AGC | 270 |
| Lys | Lys | Glu | Leu | Glu<br>85 | Gln | Glu | Leu | Ser<br>90 | |
| AAC | TTT | AAA | TCG | | | | | | 282 |
| Asn | Phe | Lys | Ser | | | | | | |

| TGAAAATGAC | AAAGATAACG | AAATTCGTGT | CATGCTCGAA | 322 |
|---|---|---|---|---|
| ATCGTCCAAC | TCAACCGTCA | GTTAAACAGC | GGCCAATTGG | 362 |
| ATTAATAACG | TTTTAAAACC | GCTAAATGAT | GGTATTATTA | 402 |
| CCTAAGAGAA | GCCTTTTAAT | AAGGTTAGCG | GCATTTTGGA | 442 |
| AGGAGGAATA | CAGGCAGTT | | | 461 |

| ATG | AGT | GAT | AAA | ACA | AAA | AAC | ACA | AAA | 488 |
|---|---|---|---|---|---|---|---|---|---|
| Met | Ser | Asp | Lys | Thr<br>95 | Lys | Asn | Thr | Lys | |

| | | | | | | | | |
|---|---|---|---|---|---|---|---|---|
| CCA<br>Pro<br>100 | GTT<br>Val | GCT<br>Ala | GAA<br>Glu | CTA<br>Leu | AGT<br>Ser<br>105 | GTT<br>Val | GAG<br>Glu | CAA<br>Gln | 515 |
| GTA<br>Val | AAA<br>Lys<br>110 | GAA<br>Glu | GCC<br>Ala | CTG<br>Leu | ATA<br>Ile | GAA<br>Glu<br>115 | GAA<br>Glu | GGT<br>Gly | 542 |
| AAG<br>Lys | AAA<br>Lys | AAG<br>Lys<br>120 | GGG<br>Gly | ATT<br>Ile | TTA<br>Leu | ACT<br>Thr | TAT<br>Tyr<br>125 | GCA<br>Ala | 569 |
| AAA<br>Lys | ATC<br>Ile | GCT<br>Ala | GCC<br>Ala<br>130 | AGA<br>Arg | TTA<br>Leu | GCT<br>Ala | CCA<br>Pro | TTC<br>Phe<br>135 | 596 |
| ACT<br>Thr | TTG<br>Leu | GAT<br>Asp | TCC<br>Ser | GAT<br>Asp<br>140 | CAA<br>Gln | ATG<br>Met | GAT<br>Asp | GAG<br>Glu | 623 |
| TAT<br>Tyr<br>145 | TTA<br>Leu | GAA<br>Glu | CAT<br>His | GTT<br>Val | GGT<br>Gly<br>150 | GAA<br>Glu | GCA<br>Ala | GGA<br>Gly | 650 |
| ATT<br>Ile | GAA<br>Glu<br>155 | GTT<br>Val | TCT<br>Ser | GAC<br>Asp | GAT<br>Asp | GCA<br>Ala<br>160 | GAT<br>Asp | GAT<br>Asp | 677 |
| GAG<br>Glu | GAT<br>Asp | CCG<br>Pro<br>165 | GAT<br>Asp | GAA<br>Glu | ACA<br>Thr | GAA<br>Glu | CTT<br>Leu<br>170 | GTA<br>Val | 704 |
| AAA<br>Lys | GAA<br>Glu | GAA<br>Glu | ACC<br>Thr<br>175 | GAA<br>Glu | TCC<br>Ser | TTT<br>Phe | GAT<br>Asp | TTA<br>Leu<br>180 | 731 |
| ACA<br>Thr | GAT<br>Asp | ATG<br>Met | AGT<br>Ser | GTA<br>Val<br>185 | CCA<br>Pro | CCA<br>Pro | GGC<br>Gly | GTA<br>Val | 758 |
| AAA<br>Lys<br>190 | ATT<br>Ile | AAT<br>Asn | GAC<br>Asp | CCT<br>Pro | GTT<br>Val<br>195 | CGC<br>Arg | ATG<br>Met | TAT<br>Tyr | 785 |
| CTG<br>Leu | AAA<br>Lys<br>200 | GAA<br>Glu | ATT<br>Ile | GGT<br>Gly | CGA<br>Arg | GTA<br>Val<br>205 | GAC<br>Asp | TTA<br>Leu | 812 |
| CTT<br>Leu | ACA<br>Thr | GCG<br>Ala<br>210 | GAT<br>Asp | GAA<br>Glu | GAA<br>Glu | ATT<br>Ile | GCC<br>Ala<br>215 | TTA<br>Leu | 839 |
| GCA<br>Ala | AAA<br>Lys | CGT<br>Arg | ATC<br>Ile<br>220 | GAA<br>Glu | GCT<br>Ala | GGC<br>Gly | GAC<br>Asp | ATT<br>Ile<br>225 | 866 |
| GAA<br>Glu | GCC<br>Ala | AAA<br>Lys | GGA<br>Gly | CGT<br>Arg<br>230 | CTT<br>Leu | GCA<br>Ala | GAA<br>Glu | GCC<br>Ala | 893 |
| AAC<br>Asn<br>235 | CTG<br>Leu | CGC<br>Arg | CTT<br>Leu | GTT<br>Val | GTA<br>Val<br>240 | AGT<br>Ser | ATT<br>Ile | GCA<br>Ala | 920 |
| AAA<br>Lys | CGT<br>Arg<br>245 | TAT<br>Tyr | GTT<br>Val | GGT<br>Gly | CGC<br>Arg | GGT<br>Gly<br>250 | ATG<br>Met | TTA<br>Leu | 947 |
| TTC<br>Phe | CTT<br>Leu | GAT<br>Asp<br>255 | TTA<br>Leu | ATT<br>Ile | CAA<br>Gln | GAA<br>Glu | GGT<br>Gly<br>260 | AAC<br>Asn | 974 |
| ATG<br>Met | GAA<br>Glu | CTA<br>Leu | ATG<br>Met<br>265 | AAA<br>Lys | GCC<br>Ala | GTT<br>Val | GAG<br>Glu | AAA<br>Lys<br>270 | 1001 |
| TTC<br>Phe | GAC<br>Asp | TTC<br>Phe | AAT<br>Asn | AAA<br>Lys<br>275 | GGA<br>Gly | TTT<br>Phe | AAA<br>Lys | TTC<br>Phe | 1028 |
| AGT<br>Ser | ACC<br>Thr | TAT<br>Tyr | GCA<br>Ala | ACG<br>Thr | | | | | 1043 |

Ser  Thr  Tyr  Ala  Thr
280

( 3 2 ) INFORMATION FOR SEQ ID NO: 31

( i ) SEQUENCE CHARACTERISTICS:
( A ) LENGTH: 277
( B ) TYPE: Nucleic acid
( C ) STRANDEDNESS: Single
( D ) TOPOLOGY: Linear ( i i ) MOLECULE TYPE: Genomic DNA ( x i ) SEQUENCE DESCRIPTION: SEQ ID NO: 31

| A AGC | TTA | ACG | GAA | GAA | CAT | GCA | GAT | TTA | 28 |
|---|---|---|---|---|---|---|---|---|---|
| Ser | Leu | Thr | Glu | Glu | His | Ala | Asp | Leu | |
| 1 | | | | 5 | | | | | |

| ATT | AAA | CGG | CTT | ACT | AAC | CGG | GCG | ATT | 55 |
|---|---|---|---|---|---|---|---|---|---|
| Ile | Lys | Arg | Leu | Thr | Asn | Arg | Ala | Ile | |
| 10 | | | | | 15 | | | | |

| ATT | TGT | TAT | GAC | GGT | GAC | AGA | GCC | GGA | 82 |
|---|---|---|---|---|---|---|---|---|---|
| Ile | Cys | Tyr | Asp | Gly | Asp | Arg | Ala | Gly | |
| | 20 | | | | | 25 | | | |

| ATT | GAA | GCA | GCC | TAT | AAG | GCG | GGC | ACG | 109 |
|---|---|---|---|---|---|---|---|---|---|
| Ile | Glu | Ala | Ala | Tyr | Lys | Ala | Gly | Thr | |
| | | 30 | | | | | 35 | | |

| CTT | CTA | GTT | GAA | CGG | AAT | CGT | TTA | GAT | 136 |
|---|---|---|---|---|---|---|---|---|---|
| Leu | Leu | Val | Glu | Arg | Asn | Arg | Leu | Asp | |
| | | | 40 | | | | | 45 | |

| GTT | TTT | GTT | TTG | CAA | CTT | CCA | GCT | GGA | 163 |
|---|---|---|---|---|---|---|---|---|---|
| Val | Phe | Val | Leu | Gln | Leu | Pro | Ala | Gly | |
| | | | | 50 | | | | | |

| AAA | GAT | CCC | GAT | GAC | TTT | ATT | CGA | GCA | 190 |
|---|---|---|---|---|---|---|---|---|---|
| Lys | Asp | Pro | Asp | Asp | Phe | Ile | Arg | Ala | |
| 55 | | | | | 60 | | | | |

| AGT | GGT | CCA | GAA | AAA | TTC | AAA | GAA | GTT | 217 |
|---|---|---|---|---|---|---|---|---|---|
| Ser | Gly | Pro | Glu | Lys | Phe | Lys | Glu | Val | |
| | | 65 | | | | 70 | | | |

| TAT | AAG | CAA | CAA | CGA | TCG | ACT | TGG | ACA | 244 |
|---|---|---|---|---|---|---|---|---|---|
| Tyr | Lys | Gln | Gln | Arg | Ser | Thr | Trp | Thr | |
| | | 75 | | | | | 80 | | |

| GCT | TTT | AAA | TTC | ATT | ATT | TAC | GTA | GAG | 271 |
|---|---|---|---|---|---|---|---|---|---|
| Ala | Phe | Lys | Phe | Ile | Ile | Tyr | Val | Glu | |
| | | | 85 | | | | | 90 | |

| AAC | GTA | | | | | | | | 277 |
|---|---|---|---|---|---|---|---|---|---|
| Asn | Val | | | | | | | | |

( 3 3 ) INFORMATION FOR SEQ ID NO: 32

( i ) SEQUENCE CHARACTERISTICS:
( A ) LENGTH: 548
( B ) TYPE: Nucleic acid
( C ) STRANDEDNESS: Single
( D ) TOPOLOGY: Linear ( i i ) MOLECULE TYPE: Genomic DNA ( x i ) SEQUENCE DESCRIPTION: SEQ ID NO: 32

| ATG | CCG | GTA | ATT | AAA | GTA | CGT | CAA | AAC | 27 |
|---|---|---|---|---|---|---|---|---|---|
| Met | Pro | Val | Ile | Lys | Val | Arg | Gln | Asn | |
| | | | | 5 | | | | | |

| GAA | TCA | TTT | GAC | GTA | GCT | TTA | CGT | CGT | 54 |
|---|---|---|---|---|---|---|---|---|---|
| Glu | Ser | Phe | Asp | Val | Ala | Leu | Arg | Arg | |
| 10 | | | | | 15 | | | | |

| TTC | AAA | CGC | TCT | TGC | GAA | AAA | GCG | GGA | 81 |
|---|---|---|---|---|---|---|---|---|---|
| Phe | Lys | Arg | Ser | Cys | Glu | Lys | Ala | Gly | |

|  |  |  |  |  |  |  |  |  |
|---|---|---|---|---|---|---|---|---|
|  | 20 |  |  |  | 25 |  |  |  |
| ATC | TTA | GCT | GAA | ATA | CGC | GCT | CGC | GAA | 108
| Ile | Leu | Ala | Glu | Ile | Arg | Ala | Arg | Glu |
|  |  | 30 |  |  |  |  | 35 |  |
| TTT | TAC | GAA | AAA | CCA | ACT | ACA | ATT | CGT | 135
| Phe | Tyr | Glu | Lys | Pro | Thr | Thr | Ile | Arg |
|  |  |  | 40 |  |  |  |  | 45 |
| AAA | CGT | GAA | AAT | GCA | ACA | CTT | GCA | AAA | 162
| Lys | Arg | Glu | Asn | Ala | Thr | Leu | Ala | Lys |
|  |  |  |  | 50 |  |  |  |  |
| CGT | CAC | GCA | AAA | CGC | AAC | GCT | CGC | GAA | 189
| Arg | His | Ala | Lys | Arg | Asn | Ala | Arg | Glu |
| 55 |  |  |  |  | 60 |  |  |  |
| AAC | GCG | CGC | AAT | ACC | CGT | TTA | TAC |  | 213
| Asn | Ala | Arg | Asn | Thr | Arg | Leu | Tyr |  |
|  | 65 |  |  |  |  | 70 |  |  |

| TAATTTATAG | TATTTTCTGA | CTCGAGTTAA | GACAAACCGT | 253 |
| GAATCCTTTG | GACTCACGGT | TTTGTTACTT | TAAGGCACAA | 293 |
| CAAAAATCTA | CGCCAAAAAC | GACCGCACTT | TCACACCACG | 333 |
| ATCACGGAGG | CTCGACA |  |  | 350 |

|  |  |  |  |  |  |  |  |  |
|---|---|---|---|---|---|---|---|---|
| ATG | AAA | GGT | TCT | ATT | CCA | CGC | CCC | TTT | 377
| Met | Lys | Gly | Ser | Ile | Pro | Arg | Pro | Phe |
|  |  |  |  | 75 |  |  |  |  |
| ATT | GAT | GAT | TTG | CTG | ACA | AAG | TCC | GAT | 404
| Ile | Asp | Asp | Leu | Leu | Thr | Lys | Ser | Asp |
| 80 |  |  |  |  | 85 |  |  |  |
| ATT | GTC | GAT | GTG | ATT | AAC | ACG | CGC | GTA | 431
| Ile | Val | Asp | Val | Ile | Asn | Thr | Arg | Val |
|  | 90 |  |  |  |  | 95 |  |  |
| AAA | CTA | AAA | AAA | GCT | GGC | CGC | GAT | TAT | 458
| Lys | Leu | Lys | Lys | Ala | Gly | Arg | Asp | Tyr |
|  |  | 100 |  |  |  |  | 105 |  |
| CAA | GCC | TGC | TGC | CCT | TTC | CAT | CAC | GAA | 485
| Gln | Ala | Cys | Cys | Pro | Phe | His | His | Glu |
|  |  |  | 110 |  |  |  |  | 115 |
| AAA | ACA | CCA | TCC | TTC | ACA | GTT | AGC | CAA | 512
| Lys | Thr | Pro | Ser | Phe | Thr | Val | Ser | Gln |
|  |  |  |  | 120 |  |  |  |  |
| AAG | AAA | CAG | TTT | TAT | CAC | TGC | TTT | GGC | 539
| Lys | Lys | Gln | Phe | Tyr | His | Cys | Phe | Gly |
| 125 |  |  |  |  | 130 |  |  |  |
| TGC | GGC | GCG |  |  |  |  |  |  | 548
| Cys | Gly | Ala |  |  |  |  |  |  |
|  | 135 |  |  |  |  |  |  |  |

( 3 4 ) INFORMATION FOR SEQ ID NO: 33

( i ) SEQUENCE CHARACTERISTICS:
        ( A ) LENGTH: 13
        ( B ) TYPE: Nucleic acid
        ( C ) STRANDEDNESS: Single
        ( D ) TOPOLOGY: Linear ( i i ) MOLECULE TYPE: Genomic DNA ( x i ) SEQUENCE DESCRIPTION: SEQ ID NO: 33

GATCACCTCC    TTA                                13

( 3 5 ) INFORMATION FOR SEQ ID NO: 34

( i ) SEQUENCE CHARACTERISTICS:
        ( A ) LENGTH: 45

(B) TYPE: Nucleic acid
(C) STRANDEDNESS: Single
(D) TOPOLOGY: Linear (ii) MOLECULE TYPE: Genomic DNA (xi) SEQUENCE DESCRIPTION: SEQ ID NO: 34

| GGCCGCCCCA | CATTGGGCAG | GTATCTGACC | AGTAGAGGGG | 40 |
| CGGCC | | | | 45 |

(36) INFORMATION FOR SEQ ID NO: 35

(i) SEQUENCE CHARACTERISTICS:
(A) LENGTH: 29
(B) TYPE: Nucleic acid
(C) STRANDEDNESS: Single
(D) TOPOLOGY: Linear (ii) MOLECULE TYPE: Genomic DNA (xi) SEQUENCE DESCRIPTION: SEQ ID NO: 35

| TTGACATAAA | TACCACTGGC | GGTGATACT | 29 |

(37) INFORMATION FOR SEQ ID NO: 36

(i) SEQUENCE CHARACTERISTICS:
(A) LENGTH: 1043
(B) TYPE: Nucleic acid
(C) STRANDEDNESS: Single
(D) TOPOLOGY: Linear (ii) MOLECULE TYPE: Genomic DNA (xi) SEQUENCE DESCRIPTION: SEQ ID NO: 36

| GCAACTTCTT | GGTGCAACAT | CGTTTATCAT | GATAATTACA | 40 |
| AAGCGCTTTA | TACCTATCTA | ATTGGTTATT | TCTGGCAGAA | 80 |
| GGTAATGATG | CAGATCCAAC | GGAAATTTAT | GGATAGTGTT | 120 |
| CCTGATGCTA | CAATGAAAGG | ACTTATCAGT | AGCCTCGAAA | 160 |
| TGGTTATTAG | TCCAGATGAA | CAAGGTAAAA | CACAGTTTGA | 200 |
| AGACTATATT | AGAAGTCTAA | AGCGGTTTAA | ATTAGAACAA | 240 |
| AAGAAAAAAG | AACTTGAGCA | AGAGCTAAGC | AACTTTAAAT | 280 |
| CGTGAAAATG | ACAAAGATAA | CGAAATTCGT | GTCATGCTCG | 320 |
| AAATCGTCCA | ACTCAACCGT | CAGTTAAACA | GCGGCCAATT | 360 |
| GGATTAATAA | CGTTTTAAAA | CCGCTAAATG | ATGGTATTAT | 400 |
| TACCTAAGAG | AAGCCTTTTA | ATAAGGTTAG | CGGCATTTTG | 440 |
| GAAGGAGGAA | TACAGGCAGT | TATGAGTGAT | AAAACAAAAA | 480 |
| ACACAAAACC | AGTTGCTGAA | CTAAGTGTTG | AGCAAGTAAA | 520 |
| AGAAGCCCTG | ATAGAAGAAG | GTAAGAAAAA | GGGGATTTTA | 560 |
| ACTTATGCAA | AAATCGCTGC | CAGATTAGCT | CCATTCACTT | 600 |
| TGGATTCCGA | TCAAATGGAT | GAGTATTTAG | AACATGTTGG | 640 |
| TGAAGCAGGA | ATTGAAGTTT | CTGACGATGC | AGATGATGAG | 680 |
| GATCCGGATG | AAACAGAACT | TGTAAAAGAA | GAAACCGAAT | 720 |
| CCTTTGATTT | AACAGATATG | AGTGTACCAC | CAGGCGTAAA | 760 |
| AATTAATGAC | CCTGTTCGCA | TGTATCTGAA | AGAAATTGGT | 800 |
| CGAGTAGACT | TACTTACAGC | GGATGAAGAA | ATTGCCTTAG | 840 |

| | | | | |
|---|---|---|---|---|
| CAAAACGTAT | CGAAGCTGGC | GACATTGAAG | CCAAAGGACG | 880 |
| TCTTGCAGAA | GCCAACCTGC | GCCTTGTTGT | AAGTATTGCA | 920 |
| AAACGTTATG | TTGGTCGCGG | TATGTTATTC | CTTGATTTAA | 960 |
| TTCAAGAAGG | TAACATGGGA | CTAATGAAAG | CCGTTGAGAA | 1000 |
| ATTCGACTTC | AATAAGGAT | TTAAATTCAG | TACCTATGCA | 1040 |
| ACG | | | | 1043 |

(38) INFORMATION FOR SEQ ID NO: 37

(i) SEQUENCE CHARACTERISTICS:
        (A) LENGTH: 277
        (B) TYPE: Nucleic acid
        (C) STRANDEDNESS: Single
        (D) TOPOLOGY: Linear (ii) MOLECULE TYPE: Genomic DNA (xi) SEQUENCE DESCRIPTION: SEQ ID NO: 37

| | | | | |
|---|---|---|---|---|
| AAGCTTAACG | GAAGAACATG | CAGATTTAAT | TAAACGGCTT | 40 |
| ACTAACCGGG | CGATTATTTG | TTATGACGGT | GACAGAGCCG | 80 |
| GAATTGAAGC | AGCCTATAAG | GCGGGCACGC | TTCTAGTTGA | 120 |
| ACGGAATCGT | TTAGATGTTT | TTGTTTTGCA | ACTTCCAGCT | 160 |
| GGAAAAGATC | CCGATGACTT | TATTCGAGCA | AGTGGTCCAG | 200 |
| AAAAATTCAA | AGAAGTTTAT | AAGCAACAAC | GATCGACTTG | 240 |
| GACAGCTTTT | AAATTCATTA | TTTACGTAGA | GAACGTA | 277 |

(39) INFORMATION FOR SEQ ID NO: 38

(i) SEQUENCE CHARACTERISTICS:
        (A) LENGTH: 548
        (B) TYPE: Nucleic acid
        (C) STRANDEDNESS: Single
        (D) TOPOLOGY: Linear (ii) MOLECULE TYPE: Genomic DNA (xi) SEQUENCE DESCRIPTION: SEQ ID NO: 38

| | | | | |
|---|---|---|---|---|
| ATGCCGGTAA | TTAAAGTACG | TCAAAACGAA | TCATTTGACG | 40 |
| TAGCTTTACG | TCGTTTCAAA | CGCTCTTGCG | AAAAAGCGGG | 80 |
| AATCTTAGCT | GAAATACGCG | CTCGCGAATT | TTACGAAAAA | 120 |
| CCAACTACAA | TTCGTAAACG | TGAAAATGCA | ACACTTGCAA | 160 |
| AACGTCACGC | AAAACGCAAC | GCTCGCGAAA | ACGCGCGCAA | 200 |
| TACCCGTTTA | TACTAATTTA | TAGTATTTTC | TGACTCGAGT | 240 |
| TAAGACAAAC | CGTGAATCCT | TTGGACTCAC | GGTTTTGTTA | 280 |
| CTTTAAGGCA | CAACAAAAT | CTACGCCAAA | AACGACCGCA | 320 |
| CTTTCACACC | ACGATCACGG | AGGCTCGACA | ATGAAAGGTT | 360 |
| CTATTCCACG | CCCCTTTATT | GATGATTTGC | TGACAAAGTC | 400 |
| CGATATTGTC | GATGTGATTA | ACACGCGCGT | AAAACTAAAA | 440 |
| AAAGCTGGCC | GCGATTATCA | AGCCTGCTGC | CCTTTCCATC | 480 |
| ACGAAAAAAC | ACCATCCTTC | ACAGTTAGCC | AAAAGAAACA | 520 |
| GTTTTATCAC | TGCTTTGGCT | GCGGCGCG | | 548 |

(40) INFORMATION FOR SEQ ID NO: 39

( i ) SEQUENCE CHARACTERISTICS:
    ( A ) LENGTH: 21
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 39

GGGATTTGCA CTAAAGCATC G　　　　　　　　　　　　　　　　　21

( 4 1 ) INFORMATION FOR SEQ ID NO: 40

( i ) SEQUENCE CHARACTERISTICS:
    ( A ) LENGTH: 20
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 40

GATCGCTTAA CCTCATCATG　　　　　　　　　　　　　　　　　20

( 4 2 ) INFORMATION FOR SEQ ID NO: 41

( i ) SEQUENCE CHARACTERISTICS:
    ( A ) LENGTH: 28
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 41

GTCGGTGTAG GAAGTTTTTC TAGGGCCG　　　　　　　　　　　28

( 4 3 ) INFORMATION FOR SEQ ID NO: 42

( i ) SEQUENCE CHARACTERISTICS:
    ( A ) LENGTH: 27
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 42

TTATCGTTGG CGGTAAACAA CCGTTGG　　　　　　　　　　　27

( 4 4 ) INFORMATION FOR SEQ ID NO: 43

( i ) SEQUENCE CHARACTERISTICS:
    ( A ) LENGTH: 18
    ( B ) TYPE: Nucleic acid
    ( C ) STRANDEDNESS: Single
    ( D ) TOPOLOGY: Linear ( i i ) MOLECULE TYPE: Genomic DNA ( x i ) SEQUENCE DESCRIPTION: SEQ ID NO: 43

GGCCCCGATT TTTAGCAA　　　　　　　　　　　　　　　　　18

( 4 5 ) INFORMATION FOR SEQ ID NO: 44

( i ) SEQUENCE CHARACTERISTICS:
    ( A ) LENGTH: 29
    ( B ) TYPE: Nucleic acid
    ( C ) STRANDEDNESS: Single
    ( D ) TOPOLOGY: Linear (i i) MOLECULE TYPE: Genomic DNA (x i) SEQUENCE DESCRIPTION: SEQ ID NO: 44

CCACGCGGAT TGGGCGTAAC GCTCTTGGG 29

(4 6) INFORMATION FOR SEQ ID NO: 45

(i) SEQUENCE CHARACTERISTICS:
        (A) LENGTH: 29
        (B) TYPE: Nucleic acid
        (C) STRANDEDNESS: Single
        (D) TOPOLOGY: Linear (i i) MOLECULE TYPE: Genomic DNA (x i) SEQUENCE DESCRIPTION: SEQ ID NO: 45

CCCAAGAGCG TTACGCCCAA TCCGCGTGG 29

(4 7) INFORMATION FOR SEQ ID NO: 46

(i) SEQUENCE CHARACTERISTICS:
        (A) LENGTH: 27
        (B) TYPE: Nucleic acid
        (C) STRANDEDNESS: Single
        (D) TOPOLOGY: Linear (i i) MOLECULE TYPE: Genomic DNA (x i) SEQUENCE DESCRIPTION: SEQ ID NO: 46

CGTGTCATGC TCGAAATCGT CCAACTC 27

(4 8) INFORMATION FOR SEQ ID NO: 47

(i) SEQUENCE CHARACTERISTICS:
        (A) LENGTH: 27
        (B) TYPE: Nucleic acid
        (C) STRANDEDNESS: Single
        (D) TOPOLOGY: Linear (i i) MOLECULE TYPE: Genomic DNA (x i) SEQUENCE DESCRIPTION: SEQ ID NO: 47

CGCCCATGCA ACCGGTTTGA GTTCGCG 27

(4 9) INFORMATION FOR SEQ ID NO: 48

(i) SEQUENCE CHARACTERISTICS:
        (A) LENGTH: 24
        (B) TYPE: Nucleic acid
        (C) STRANDEDNESS: Single
        (D) TOPOLOGY: Linear (i i) MOLECULE TYPE: Genomic DNA (x i) SEQUENCE DESCRIPTION: SEQ ID NO: 48

CGGCGCTTAC GCAAGTCAGC GACA 24

(5 0) INFORMATION FOR SEQ ID NO: 49

(i) SEQUENCE CHARACTERISTICS:
        (A) LENGTH: 22
        (B) TYPE: Nucleic acid
        (C) STRANDEDNESS: Single
        (D) TOPOLOGY: Linear (i i) MOLECULE TYPE: Genomic DNA (x i) SEQUENCE DESCRIPTION: SEQ ID NO: 49

CGACAGCTAT ACCGTCGACA CC 22

(51) INFORMATION FOR SEQ ID NO: 50

(i) SEQUENCE CHARACTERISTICS:
(A) LENGTH: 190
(B) TYPE: Amino acid
(C) STRANDEDNESS: Single
(D) TOPOLOGY: Linear (ii) MOLECULE TYPE: Genomic DNA (xi) SEQUENCE DESCRIPTION: SEQ ID NO: 50

| Ala 1 | Thr | Ser | Trp | Cys 5 | Asn | Ile | Val | Tyr | His 10 | Asp | Asn |
| --- | --- | --- | --- | --- | --- | --- | --- | --- | --- | --- | --- |
| Tyr | Lys | Ala 15 | Leu | Tyr | Thr | Tyr | Leu 20 | Ile | Gly | Tyr | Phe |
| Trp 25 | Gln | Lys | Val | Met | Met 30 | Gln | Ile | Gln | Arg | Lys 35 | Phe |
| Met | Asp | Ser | Val 40 | Pro | Asp | Ala | Thr | Met 45 | Lys | Gly | Leu |
| Ile | Ser 50 | Ser | Leu | Glu | Met | Val 55 | Ile | Ser | Pro | Asp | Glu 60 |
| Gln | Gly | Lys | Thr | Gln 65 | Phe | Glu | Asp | Tyr | Ile 70 | Arg | Ser |
| Leu | Lys | Arg 75 | Phe | Lys | Leu | Glu | Gln 80 | Lys | Lys | Lys | Glu |
| Leu 85 | Glu | Gln | Glu | Leu | Ser 90 | Asn | Phe | Lys | Ser | | |
| MET | Ser | Asp | Lys | Thr 5 | Lys | Asn | Thr | Lys | Pro 10 | Val | Ala |
| Glu | Leu | Ser 15 | Val | Glu | Gln | Val | Lys 20 | Glu | Ala | Leu | Ile |
| Glu 25 | Glu | Gly | Lys | Lys | Lys 30 | Gly | Ile | Leu | Thr | Tyr 35 | Ala |
| Lys | Ile | Ala | Ala 40 | Arg | Leu | Ala | Pro | Phe 45 | Thr | Leu | Asp |
| Ser | Asp 50 | Gln | MET | Asp | Glu | Tyr 55 | Leu | Glu | His | Val | Gly 60 |
| Glu | Ala | Gly | Ile | Glu 65 | Val | Ser | Asp | Asp | Ala 70 | Asp | Asp |
| Glu | Asp | Pro 75 | Asp | Glu | Thr | Glu | Leu 80 | Val | Lys | Glu | Glu |
| Thr 85 | Glu | Ser | Phe | Asp | Leu 90 | Thr | Asp | MET | Ser | Val 95 | Pro |
| Pro | Gly | Val | Lys 100 | Ile | Asn | Asp | Pro | Val 105 | Arg | MET | Tyr |
| Leu | Lys 110 | Glu | Ile | Gly | Arg | Val 115 | Asp | Leu | Leu | Thr | Ala 120 |
| Asp | Glu | Glu | Ile | Ala 125 | Leu | Ala | Lys | Arg | Ile 130 | Glu | Ala |
| Gly | Asp | Ile 135 | Glu | Ala | Lys | Gly | Arg 140 | Leu | Ala | Glu | Ala |
| Asn 145 | Leu | Arg | Leu | Val | Val 150 | Ser | Ile | Ala | Lys | Arg 155 | Tyr |
| Val | Gly | Arg | Gly 160 | MET | Leu | Phe | Leu | Asp 165 | Leu | Ile | Gln |
| Glu | Gly 170 | Asn | MET | Gly | Leu | MET 175 | Lys | Ala | Val | Glu | Lys 180 |
| Phe | Asp | Phe | Asn | Lys | Gly | Phe | Lys | Phe | Ser | Thr | Tyr |

185                              190

Ala    Thr ( 5 2 ) INFORMATION FOR SEQ ID NO: 51

( i ) SEQUENCE CHARACTERISTICS:
                ( A ) LENGTH: 90
                ( B ) TYPE: Amino acid
                ( C ) STRANDEDNESS: Single
                ( D ) TOPOLOGY: Linear ( i i ) MOLECULE TYPE: Genomic DNA ( x i ) SEQUENCE DESCRIPTION: SEQ ID NO: 51

Ser    Leu    Thr    Glu    Glu    His    Ala    Asp    Leu    Ile    Lys    Arg
1                           5                                          10

Leu    Thr    Asn    Arg    Ala    Ile    Ile    Cys    Tyr    Asp    Gly    Asp
              15                                  20

Arg    Ala    Gly    Ile    Glu    Ala    Ala    Tyr    Lys    Ala    Gly    Thr
25                                  30                                 35

Leu    Leu    Val    Glu    Arg    Asn    Arg    Leu    Asp    Val    Phe    Val
                     40                                  45

Leu    Gln    Leu    Pro    Ala    Gly    Lys    Asp    Pro    Asp    Asp    Phe
       50                                  55                                 60

Ile    Arg    Ala    Ser    Gly    Pro    Glu    Lys    Phe    Lys    Glu    Val
                            65                                  70

Tyr    Lys    Gln    Gln    Arg    Ser    Thr    Trp    Thr    Ala    Phe    Lys
              75                                  80

Phe    Ile    Ile    Tyr    Val    Glu    Asn    Val
85                                  90

( 5 3 ) INFORMATION FOR SEQ ID NO: 52

( i ) SEQUENCE CHARACTERISTICS:
                ( A ) LENGTH: 55
                ( B ) TYPE: Amino acid
                ( C ) STRANDEDNESS: Single
                ( D ) TOPOLOGY: Linear ( i i ) MOLECULE TYPE: Genomic DNA ( x i ) SEQUENCE DESCRIPTION: SEQ ID NO: 52

Met    Pro    Val    Ile    Lys    Val    Arg    Glu    Asn    Glu    Ser    Phe
                            5                                          10

Asp    Val    Ala    Leu    Arg    Arg    Phe    Lys    Arg    Ser    Cys    Glu
              15                                  20

Lys    Ala    Gly    Ile    Leu    Ala    Glu    Ile    Arg    Ala    Arg    Glu
25                                  30                                 35

Phe    Tyr    Glu    Lys    Pro    Thr    Thr    Ile    Arg    Lys    Arg    Glu
                     40                                  45

Asn    Ala    Thr    Leu    Ala    Lys    Arg    His    Ala    Lys    Arg    Asn
       50                                  55                                 60

Ala    Arg    Glu    Asn    Ala    Arg    Asn    Thr    Arg    Leu    Tyr
                            65                                  70

Met    Lys    Gly    Ser    Ile    Pro    Arg
              75

Pro    Phe    Ile    Asp    Asp    Leu    Leu    Thr    Lys    Ser    Asp    Ile
1                           5                                          10

Val    Asp    Val    Ile    Asn    Thr    Arg    Vel    Lys    Leu    Lys    Lys
              15                                  20

Ala    Gly    Arg    Asp    Tyr    Gln    Ala    Cys    Cys    Pro    Phe    His

|  | 25 |  |  | 30 |  |  |  | 35 |  |  |
|---|---|---|---|---|---|---|---|---|---|---|
| His | Glu | Lys | Thr | Pro | Ser | Phe | Thr | Val | Ser | Gln | Lys |
|  |  |  | 40 |  |  |  |  | 45 |  |  |
| Lys | Gln | Phe | Tyr | His | Cys | Phe | Gly | Cys | Gly | Ala |
|  | 50 |  |  |  |  | 55 |  |  |  |  |